US012788211B2

(12) United States Patent
Tanigami et al.

(10) Patent No.: US 12,788,211 B2
(45) Date of Patent: Nov. 10, 2026

(54) ASSISTANT DEVICE, ENDOSCOPIC SYSTEM, ASSISTANT METHOD, AND COMPUTER-READABLE RECORDING MEDIUM

(71) Applicant: OLYMPUS CORPORATION, Tokyo (JP)

(72) Inventors: Yasuo Tanigami, Tokyo (JP); Yusuke Otsuka, Yokohama (JP); Noriko Kuroda, Machida (JP); Takaaki Igarashi, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 744 days.

(21) Appl. No.: 18/127,051

(22) Filed: Mar. 28, 2023

(65) Prior Publication Data

US 2023/0248209 A1 Aug. 10, 2023

Related U.S. Application Data

(63) Continuation of application No. PCT/JP2020/036993, filed on Sep. 29, 2020.

(51) Int. Cl.
*A61B 1/00* (2006.01)
*A61B 1/04* (2006.01)
(Continued)

(52) U.S. Cl.
CPC .... *A61B 1/000094* (2022.02); *A61B 1/00096* (2013.01); *A61B 1/043* (2013.01);
(Continued)

(58) Field of Classification Search
CPC .......... A61B 1/000094; A61B 1/00096; A61B 1/043; A61B 1/05; A61B 1/0661;
(Continued)

(56) References Cited

U.S. PATENT DOCUMENTS

2009/0043303 A1 2/2009 Shimomura
2010/0063496 A1 3/2010 Trovato et al.
(Continued)

FOREIGN PATENT DOCUMENTS

CN 105744883 A 7/2016
JP 2008-246111 A 10/2008
(Continued)

OTHER PUBLICATIONS

Japanese Office Action dated Aug. 19, 2024 received in 2022-553275.
(Continued)

*Primary Examiner* — Michael J Carey
*Assistant Examiner* — William B Chou
(74) *Attorney, Agent, or Firm* — Scully, Scott, Murphy & Presser, P.C.

(57) ABSTRACT

An assistant device includes a processor configured to: generate a first image including one or more characteristic regions requiring excision by a surgical operator; generate a second image including one or more cauterized regions cauterized by an energy device; generate information regarding presence or absence of a first region that is included in the characteristic regions and that is not included in the cauterized region based on the first image and the second image; and output information indicating the presence of the characteristic regions that requires to be cauterized when the first region is present.

14 Claims, 26 Drawing Sheets

(51) Int. Cl.

| | |
|---|---|
| ***A61B 1/05*** | (2006.01) |
| ***A61B 1/06*** | (2006.01) |
| ***G06T 7/00*** | (2017.01) |

(52) U.S. Cl.

CPC .............. *A61B 1/05* (2013.01); *A61B 1/0661* (2013.01); *G06T 7/0014* (2013.01); *G06T 2207/10064* (2013.01); *G06T 2207/10068* (2013.01); *G06T 2207/20081* (2013.01); *G06T 2207/30096* (2013.01)

(58) Field of Classification Search

CPC ......... G06T 7/0014; G06T 2207/10064; G06T 2207/10068; G06T 2207/20081; G06T 2207/30096

See application file for complete search history.

(56) References Cited

U.S. PATENT DOCUMENTS

| | | | |
|---|---|---|---|
| 2011/0015628 | A1 | 1/2011 | Dalal et al. |
| 2014/0030534 | A1 | 1/2014 | Carlson et al. |
| 2015/0018807 | A1 | 1/2015 | Kircher et al. |
| 2015/0141847 | A1 | 5/2015 | Sarvazyan |
| 2015/0305604 | A1 | 10/2015 | Melsky |
| 2016/0000329 | A1 | 1/2016 | Kircher et al. |
| 2017/0014202 | A1 | 1/2017 | Ransbury et al. |
| 2018/0025481 | A1 | 1/2018 | Onimura et al. |
| 2019/0150718 | A1 | 5/2019 | Melsky |
| 2020/0008681 | A1 | 1/2020 | Sarvazyan |
| 2021/0045834 | A1 | 2/2021 | Ransbury et al. |
| 2021/0186594 | A1 | 6/2021 | Tanigami et al. |
| 2021/0386270 | A1* | 12/2021 | Tanigami ............. A61B 1/0655 |
| 2023/0225804 | A1* | 7/2023 | Azizian .................. A61B 34/25 715/771 |

FOREIGN PATENT DOCUMENTS

| | | | |
|---|---|---|---|
| JP | 2010-516371 | A | 5/2010 |
| JP | 2010099193 | A | 5/2010 |
| JP | 2011200534 | A | 10/2011 |
| JP | 2016-043128 | A | 4/2016 |
| JP | 2016-510109 | A | 4/2016 |
| JP | 2017-500550 | A | 1/2017 |
| JP | 2017-023604 | A | 2/2017 |
| JP | 2017-513645 | A | 6/2017 |
| JP | 2018-520795 | A | 8/2018 |
| WO | 2016/158593 | A1 | 10/2016 |
| WO | 2020/054723 | A1 | 3/2020 |

OTHER PUBLICATIONS

International Search Report dated Dec. 15, 2020 received in PCT/JP2020/036993.

Chinese Office Action dated May 23, 2025 received in 202080105629.6.

* cited by examiner

ASSISTANT DEVICE, ENDOSCOPIC SYSTEM, ASSISTANT METHOD, AND COMPUTER-READABLE RECORDING MEDIUM

CROSS-REFERENCE TO RELATED APPLICATION

This application is a continuation of International Application No. PCT/JP2020/036993, filed on Sep. 29, 2020, the entire contents of which are incorporated herein by reference.

BACKGROUND

1. Technical Field

The present disclosure relates to an assistant device, endoscopic system, assistant method, and computer-readable recording medium, which performs image processing on an imaging signal obtained by capturing a subject and outputs the result accordingly.

2. Related Art

The technique of transurethral resection of bladder tumors (TUR-Bt) is known in the related art, where a surgical endoscope (resectoscope) is inserted through the urethra of a subject. Then, a surgical operator uses an excision treatment instrument such as an energy device to excise a living tissue including a nidus site, while observing the nidus site through the eyepiece of the surgical endoscope (see, e.g., JP2008-246111A).

SUMMARY

In some embodiments, an assistant device includes a processor configured to: generate a first image including one or more characteristic regions requiring excision by a surgical operator; generate a second image including one or more cauterized regions cauterized by an energy device; generate information regarding presence or absence of a first region that is included in the characteristic regions and that is not included in the cauterized region based on the first image and the second image; and output information indicating the presence of the characteristic regions that requires to be cauterized when the first region is present.

In some embodiments, an endoscopic system includes: an endoscope configured to be insert into a lumen of a subject; a light source configured to apply excitation light that excites advanced glycation end products produced by subjecting a living tissue to thermal treatment; and a controller that is be detachable from the endoscope, the endoscope including an image sensor and an optical filter, the image sensor being configured to generate an imaging signal by capturing fluorescence emitted by the excitation light, the optical filter being provided on a light-receiving surface side of the image sensor, the optical filter being configured to block light on a short wavelength side including a part of a wavelength band of the excitation light, the controller including a processor configured to: generate a first image including one or more characteristic regions requiring excision by a surgical operator; generate a second image including one or more cauterized regions cauterized by an energy device; generate information regarding presence or absence of a first region that is included in the characteristic regions and that is not included in the cauterized region based on the first image and the second image; and output information indicating the presence of the characteristic regions that requires to be cauterized when the first region is present.

In some embodiments, provided is an assistant method executed by an assistant device. The method includes: generating a first image including one or more characteristic regions requiring excision by a surgical operator; generating a second image including one or more cauterized regions cauterized by an energy device; generating information regarding presence or absence of a first region that is included in the characteristic regions and that is not included in the cauterized region based on the first image and the second image; and outputting information indicating the presence of the characteristic regions that requires to be cauterized when the first region is present.

In some embodiments, a non-transitory computer-readable recording medium with an executable program stored thereon, the program causing an assistant device to: generate a first image including one or more characteristic regions requiring excision by a surgical operator; generate a second image including one or more cauterized regions cauterized by an energy device; generate information regarding presence or absence of a first region that is included in the characteristic regions and that is not included in the cauterized region based on the first image and the second image; and output information indicating the presence of the characteristic regions that requires to be cauterized when the first region is present.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
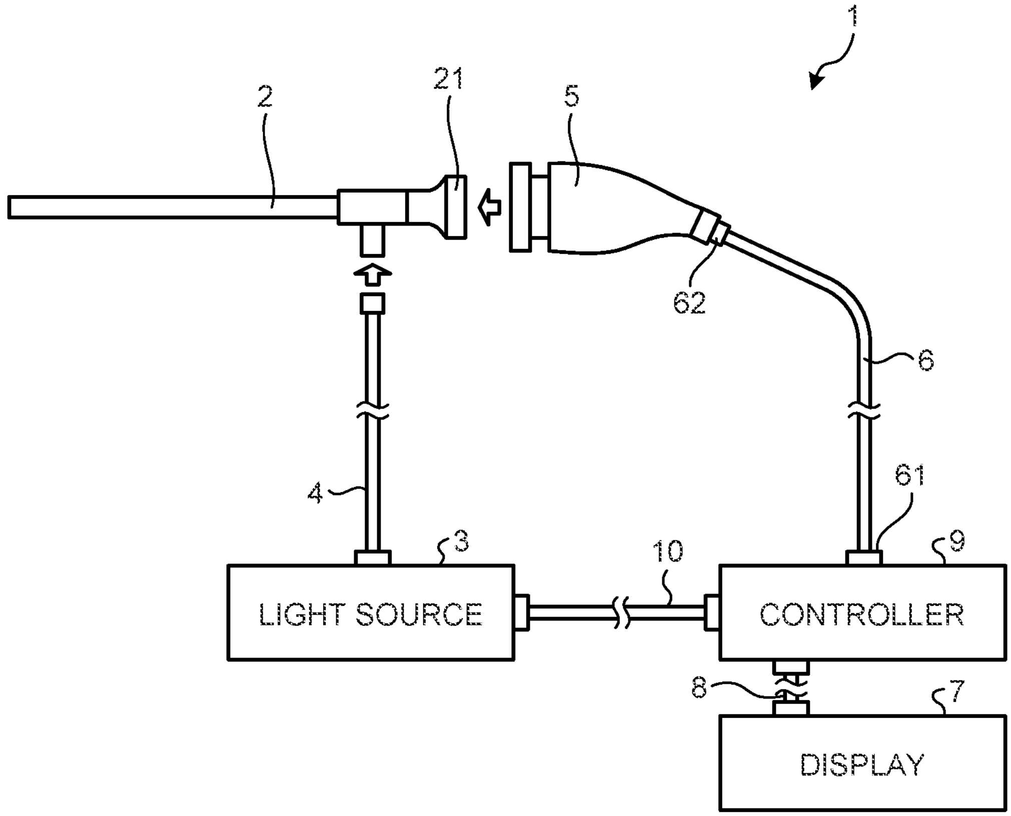
FIG. 1 is a diagram illustrating an overview configuration of an endoscopic system according to a first embodiment.

Embodiments for carrying out the present disclosure are now described in detail with reference to drawings. Moreover, the present disclosure should not be construed as being limited to the following embodiments. In addition, each drawing referred to in the following description only schematically illustrates the shape, dimension, and relative positional relationship to the extent that the contents of the present disclosure can be understood. In other words, the present disclosure should not be construed as being limited only to the shapes, dimensions, and relative positional relationships illustrated in each drawing. Furthermore, in the description with reference to the drawings, the same parts are denoted by the same reference numerals. Moreover, an endoscopic system provided with a rigid endoscope and a medical imaging device will be described as an example of an endoscopic system according to the present disclosure.

First Embodiment

Configuration of Endoscopic System

FIG. 1 is a diagram illustrating an overview configuration of an endoscopic system according to a first embodiment. The endoscopic system 1 illustrated in FIG. 1 is used for image observation of living tissues in a subject, such as a living body, in the medical field. Moreover, although the first embodiment describes, as the endoscopic system 1, a rigid endoscopic system using a rigid endoscope (an insertion portion 2) illustrated in FIG. 1, the arrangement of the embodiment is not limited to this exemplary configuration. In one example, an endoscopic system provided with a flexible endoscope can be employed. Furthermore, the endoscopic system 1 can be applied to a system provided with a medical imaging device that captures an image of a subject to perform surgery, treatment, or the like while displaying an observation image on a display. The observation image is based on image data captured by the medical imaging device. In addition, the endoscopic system 1 illustrated in FIG. 1 is used for surgery or treatment on the subject using a treatment instrument (not illustrated) such as an energy device, which subjects the subject to thermal treatment. Specifically, the endoscopic system 1 illustrated in FIG. 1 is used for the transurethral resection of bladder tumors (TUR-Bt), treating bladder tumors (bladder cancer) or lesion sites.

The endoscopic system 1 illustrated in FIG. 1 includes an insertion portion 2, a light source 3, a light guide 4, an endoscopic camera head 5 (an endoscopic imaging device), a first transmission cable 6, a display 7, a second transmission cable 8, a controller 9, and a third transmission cable 10.

The insertion portion 2 has a rigid or at least partially flexible elongated shape. The insertion portion 2 is inserted into a subject of a patient or the like through a trocar. The insertion portion 2 is provided therein with an optical system including a lens for forming an image for observation.

The light source 3 is connected to one end of the light guide 4 and supplies illumination light to be applied to a subject on one end of the light guide 4 under the control of the controller 9. The light source 3 is implemented employing a light source, a processor, and a memory. The light source of the light source 3 is one or more light sources such as a light-emitting diode (LED) light source, a xenon lamp, and a semiconductor laser device, including a laser diode (LD). The processor is a processing device that includes hardware such as a field programmable gate array (FPGA) or central processing unit (CPU), while the memory is a temporary storage area for the processor. Moreover, the light source 3 and the controller 9 can communicate separately, as illustrated in FIG. 1, or can be integrated.

The light guide 4 has one end detachably connected to the light source 3 and the other end detachably connected to the insertion portion 2. The light guide 4 guides illumination light supplied from the light source 3 from one end thereof to the other end to be supplied to the insertion portion 2.

The endoscopic camera head 5 is detachably connected to an eyepiece 21 of the insertion portion 2. The endoscopic camera head 5 receives an observation image formed by the insertion portion 2 and subjects the received light to photoelectric conversion to generate an imaging signal (raw data), and outputs the imaging signal to the controller 9 via the first transmission cable 6, under the control of the controller 9.

The first transmission cable 6 has one end detachably connected to the controller 9 via a video connector 61 and the other end detachably connected to the endoscopic camera head 5 via a camera head connector 62. The first transmission cable 6 transmits an imaging signal output from the endoscopic camera head 5 to the controller 9 and transmits setting data, electric power, or the like that is output from the controller 9 to the endoscopic camera head 5. The setting data is herein a control signal, synchronization, clock, or similar signals used to control the endoscopic camera head 5.

The display 7 displays an observation image and various types of information under the control of the controller 9. The observation image is based on an imaging signal subjected to image processing in the controller 9. The various types of information are related to the endoscopic system 1. The display 7 is implemented employing a monitor of liquid crystal display, organic electroluminescence (EL) display, or the like.

The second transmission cable 8 has one end detachably connected to the display 7 and the other end detachably connected to the controller 9. The second transmission cable 8 transmits the imaging signal subjected to image processing by the controller 9 to the display 7.

The controller 9 is implemented employing a processor and a memory. The processor in the controller 9 is a processing device having the hardware of a graphics processing unit (GPU), FPGA, CPU, or the like. The memory is a temporary storage area used by the processor. The controller 9 centrally controls operations of the endoscopic camera head 5, the display 7, and the light source 3 via the first transmission cable 6, the second transmission cable 8, and the third transmission cable 10, respectively, in accordance with a program recorded in the memory. In addition, the controller 9 performs various types of image processing on the imaging signal that is input via the first transmission cable 6 and outputs the processed imaging signal to the second transmission cable 8.

The third transmission cable 10 has one end detachably connected to the light source 3 and the other end detachably connected to the controller 9. The third transmission cable 10 transmits control data from the controller 9 to the light source 3.

Functional Configuration of Main Components of Endoscopic System

Figure 2:
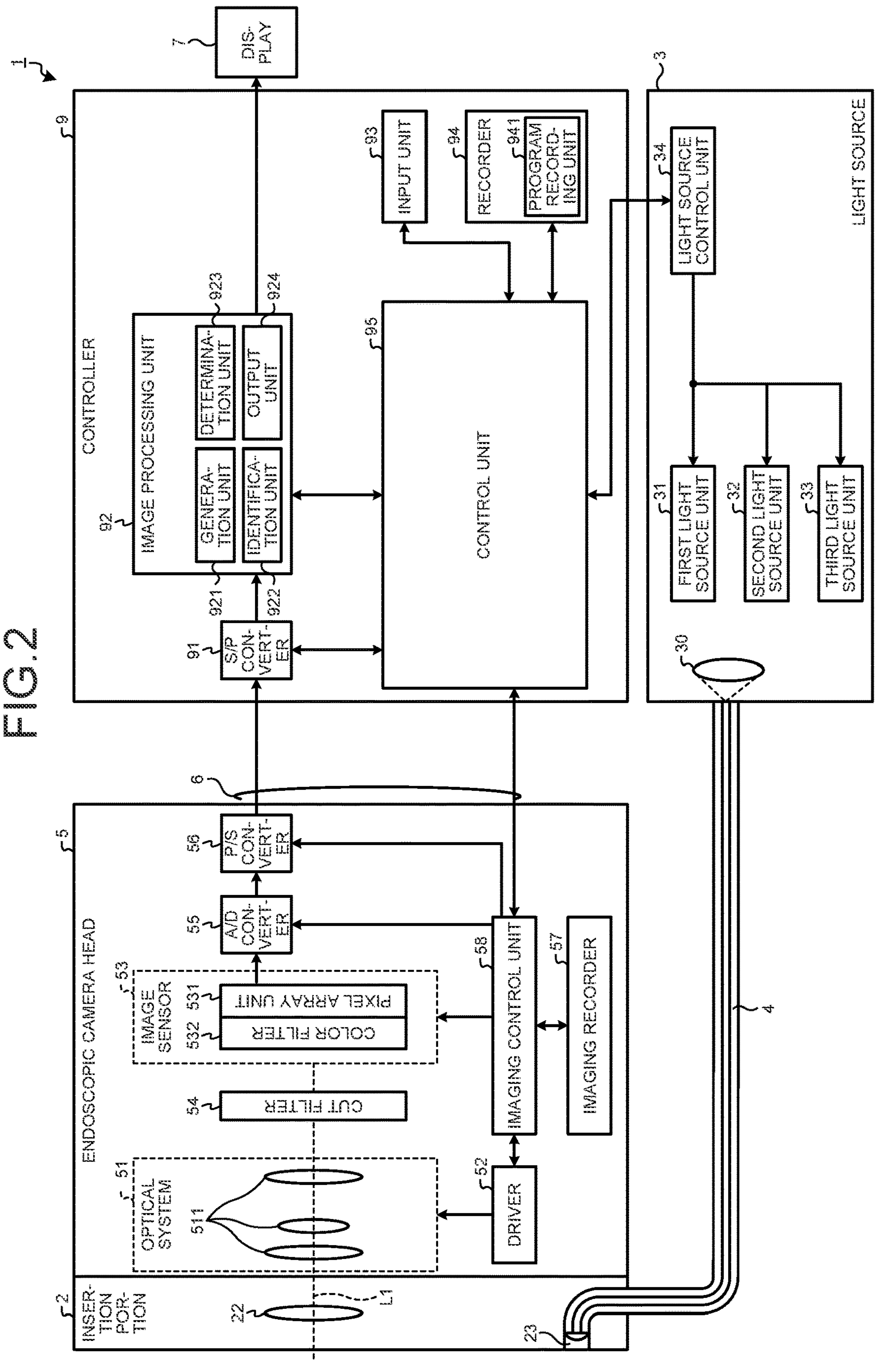
FIG. 2 is a block diagram illustrating a functional configuration of main components of the endoscopic system according to the first embodiment.

Next, a functional configuration of main components of the above-described endoscopic system 1 will be described. FIG. 2 is a block diagram illustrating a functional configuration of main components of the endoscopic system 1.

Configuration of Insertion Portion

The configuration of the insertion portion 2 is now described. The insertion portion 2 has an optical system 22 and an illumination optical system 23.

The optical system 22 converges light including reflected light that is reflected from a photographic subject, return light from the photographic subject, excitation light from the photographic subject, light emitted by the subject, or the like to form a photographic subject image. The optical system 22 is implemented employing one or more lenses or similar components.

The illumination optical system 23 irradiates the photographic subject with illumination light supplied through the light guide 4. The illumination optical system 23 is implemented employing one or more lenses or similar components.

Configuration of Light Source

The configuration of the light source 3 is now described. The light source 3 includes a condenser lens 30, a first light source unit 31, a second light source unit 32, a third light source unit 33, and a light source control unit 34.

The condenser lens 30 converges each ray of light emitted from the first light source unit 31, the second light source unit 32, and the third light source unit 33 and emits the light through the light guide 4.

The first light source unit 31 emits visible white light (normal light) to cause the light guide 4 to be supplied with the white light as illumination light, which is performed under the control of the light source control unit 34. The first light source unit 31 includes a collimator lens, a white LED lamp, a driver, and similar components. Moreover, the first light source unit 31 can supply a visible wavelength spectrum of white light by simultaneous emission of light using a red LED lamp, a green LED lamp, and a blue LED lamp. The first light source unit 31 can be configured to use a halogen lamp, a xenon lamp, or similar components.

The second light source unit 32 emits a first narrow-band light beam with a predetermined wavelength band to cause the light guide 4 to be supplied with the first narrow-band light beam as illumination light, which is performed under the control of the light source control unit 34. The first narrow-band light beam herein has a wavelength band ranging from 530 to 550 nanometers (nm) (with a central wavelength of 540 nm). The second light source unit 32 uses a green LED lamp, a collimator lens, a transmission filter that allows light with a wavelength ranging from 530 nm to 550 nm to pass, a driving driver, and the like.

The third light source unit 33 emits a second narrow-band light beam with a wavelength band different from that of the first narrow-band light beam, causing the light guide 4 to be supplied with the second narrow-band light beam as illumination light, which is performed under the control of the light source control unit 34. The second narrow-band light beam herein has a wavelength band ranging from 400 nm to 430 nm (with a central wavelength of 415 nm). The third light source unit 33 is implemented employing a collimator lens, a semiconductor laser such as a violet laser diode (LD), a driver, and similar components. Moreover, in the first embodiment, the second narrow-band light beam functions as excitation light to excite advanced glycation end products that are produced by living tissue subjected to thermal treatment.

The light source control unit 34 is implemented employing a processor and a memory. The processor is a processing device that includes hardware such as an FPGA or CPU, while the memory is a temporary storage area for the processor. The light source control unit 34 controls the timing, duration, or the like of light emission for the first light source unit 31, the second light source unit 32, and the third light source unit 33 on the basis of the control data that is input from the controller 9.

Figure 3:
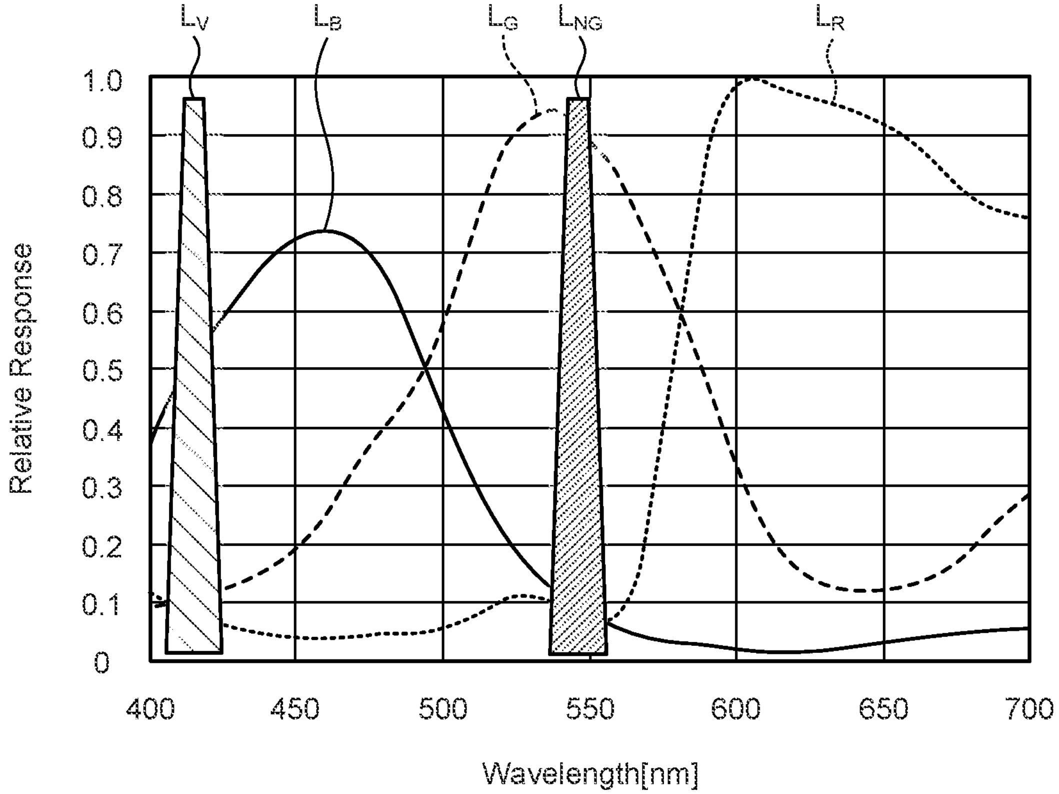
FIG. 3 is a diagram schematically illustrating wavelength characteristics of light emitted from each of a second light source unit and a third light source unit according to the first embodiment.

Wavelength characteristics of light emitted from each of the second light source unit 32 and the third light source unit 33 are now described. FIG. 3 is a diagram schematically illustrating wavelength characteristics of light emitted by each of the second light source unit 32 and the third light source unit 33. In FIG. 3, the horizontal axis indicates wavelength measured in nanometers (nm), and the vertical axis indicates wavelength characteristics. Furthermore, in FIG. 3, polygonal line $L_{NG}$ indicates the wavelength characteristics of the first narrow-band light beam emitted by the second light source unit 32, and polygonal line $L_V$ indicates the wavelength characteristics of the second narrow-band light beam (excitation light) emitted by the third light source unit 33. Moreover, in FIG. 3, curve $L_B$ indicates the blue wavelength band, curve $L_G$ indicates the green wavelength band, and curve $L_R$ indicates the red wavelength band.

In FIG. 3, the polygonal line $L_{NG}$ indicates that the second light source unit 32 emits the narrow-band light with a central wavelength (peak wavelength) of 540 nm and a wavelength band ranging from 530 nm to 550 nm. While, the third light source unit 33 emits excitation light with a central wavelength (peak wavelength) of 415 nm and a wavelength band ranging from 400 nm to 430 nm.

Thus, the second light source unit 32 and the third light source unit 33 emit the first narrow-band light beam and the second narrow-band light beam (excitation light), respectively, in different wavelength bands.

Configuration of Endoscopic Camera Head

Referring back to FIG. 2, the description of the configuration of the endoscopic system 1 continues.

The configuration of the endoscopic camera head 5 is now described. The endoscopic camera head 5 includes an optical system 51, a driver 52, an image sensor 53, a cut filter 54, an analog-to-digital (A/D) converter 55, a parallel-to-serial (P/S) converter 56, an imaging recorder 57, and an imaging control unit 58.

The optical system 51 forms a photographic subject image condensed by the optical system 22 of the insertion portion 2 on a light-receiving surface of the image sensor 53. The optical system 51 is capable of modifying the focal length and focal position. The optical system 51 includes a plurality of lenses 511. The optical system 51 changes the focal length and position by causing the driver 52 to move each of the plurality of lenses 511 along an optical axis L1.

The driver 52 shifts the plurality of lenses 511 of the optical system 51 along the optical axis L1 under the control of the imaging control unit 58. The driver 52 includes a motor and a transmission mechanism. Examples of the motor include a stepping motor, a DC motor, and a voice coil motor. The transmission mechanism can be a gear or the like that transmits the rotation of the motor to the optical system 51.

The image sensor 53 is implemented employing a charge-coupled device (CCD) or complementary metal-oxide-semiconductor (CMOS) image sensor having a plurality of pixels arranged in a two-dimensional matrix. The image sensor 53 receives the photographic subject image (rays of light), which is formed by the optical system 51 and passes through the cut filter 54, subjects the received image to photoelectric conversion to generate an imaging signal (raw data), and outputs the generated image to the A/D converter 55, which is performed under the control of the imaging control unit 58. The image sensor 53 has a pixel array unit 531 and a color filter 532.

Figure 4:
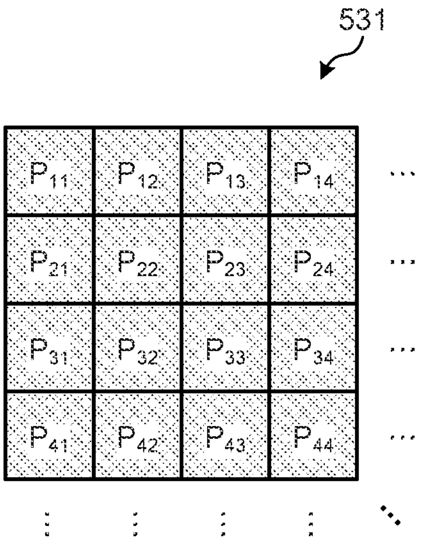
FIG. 4 is a diagram schematically illustrating a configuration of a pixel array unit according to the first embodiment.

FIG. 4 is a diagram schematically illustrating the configuration of the pixel array unit 531. As illustrated in FIG. 4, the pixel array unit 531 has a plurality of pixels $P_{nm}$ (where n is an integer of one or more, and m is an integer of one or more) arranged in a two-dimensional matrix. Examples of the pixel include a photodiode for accumulating charges depending on the quantity or intensity of light. The pixel array unit 531 reads an imaging signal as image data from a pixel $P_{nm}$ in a readout region optionally set as a readout target among the plurality of pixels $P_{nm}$ and outputs the imaging signal to the A/D converter 55, which is performed under the control of the imaging control unit 58.

Figure 5:
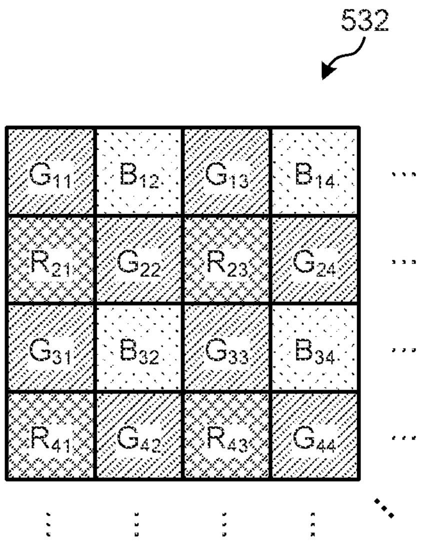
FIG. 5 is a diagram schematically illustrating a configuration of a color filter according to the first embodiment.

FIG. 5 is a diagram schematically illustrating the configuration of the color filter 532. As illustrated in FIG. 5, the color filter 532 is configured in a Bayer pattern with 2×2 as one constituent unit. The color filter 532 includes an R-filter, two G-filters, and a B-filter. The R-filter passes light in the red wavelength band, the G-filter passes light in the green wavelength band, and the B-filter passes light in the blue wavelength band.

Figure 6:
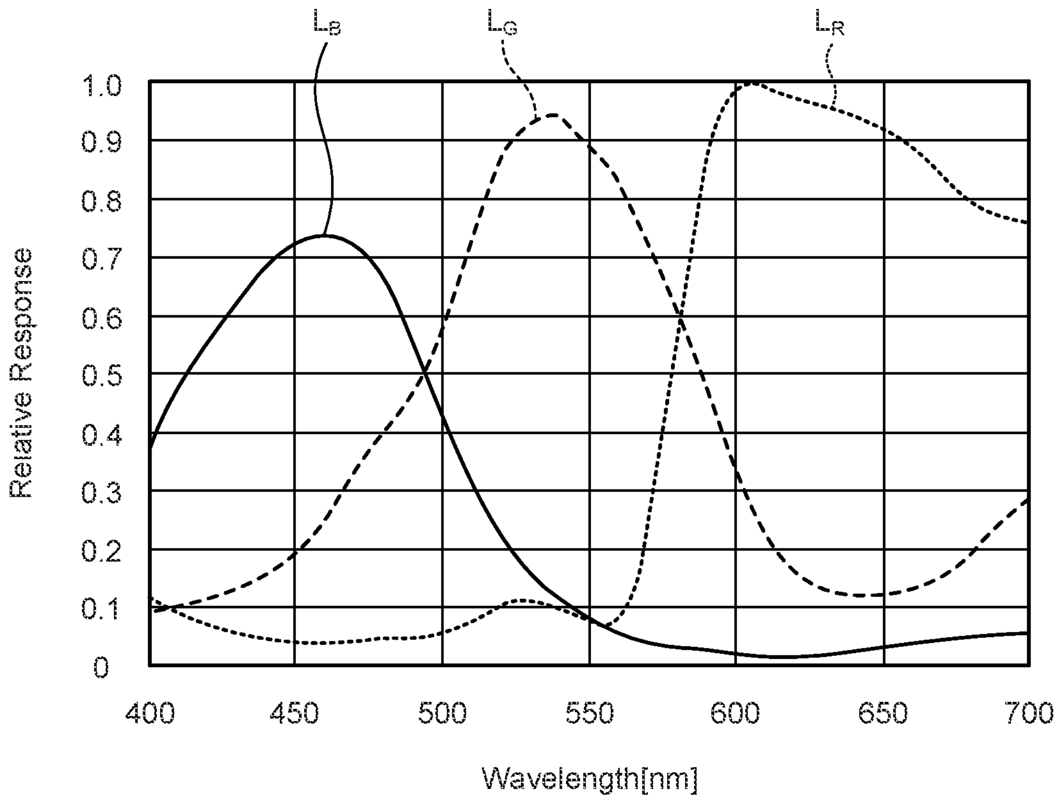
FIG. 6 is a diagram schematically illustrating the sensitivity and wavelength band of each filter.

FIG. 6 is a diagram schematically illustrating the sensitivity and wavelength band of each filter. In FIG. 6, the horizontal axis indicates the wavelength (nm), and the vertical axis indicates the transmission characteristics (sensitivity characteristics). Furthermore, in FIG. 6, curve $L_B$ indicates the transmission characteristics of the B-filter, curve $L_G$ indicates the transmission characteristics of the G-filter, and curve $L_R$ indicates the transmission characteristics of the R-filter.

As indicated by curve $L_B$ in FIG. 6, the B-filter passes light in the blue wavelength band. In addition, as indicated by curve $L_G$ in FIG. 6, the G-filter passes light in the green wavelength band. Furthermore, as indicated by curve $L_R$ in FIG. 6, the R-filter passes light in the red wavelength band. Moreover, the following description is given assuming that a pixel $P_{nm}$ having the R-filter arranged on the light-receiving surface is referred to as an R pixel, a pixel $P_{nm}$ having the G-filter arranged on the light-receiving surface is referred to as a G pixel, and a pixel $P_{nm}$ having the B-filter arranged on the light-receiving surface is referred to as a B pixel.

Figure 7A:
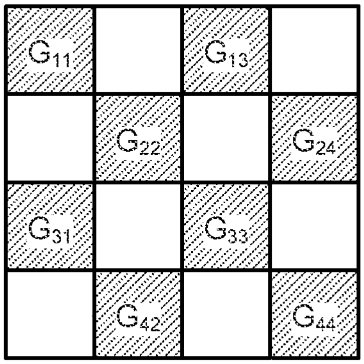
FIG. 7A is a diagram schematically illustrating a signal value of R pixel in an image sensor according to the first embodiment.
Figure 7B:
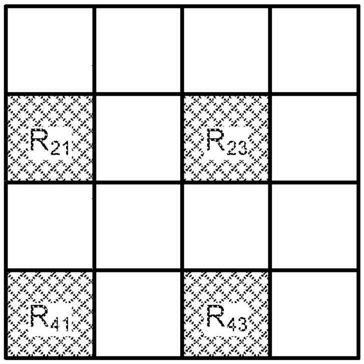
FIG. 7B is a diagram schematically illustrating a signal value of G pixel in an image sensor according to the first embodiment.
Figure 7C:
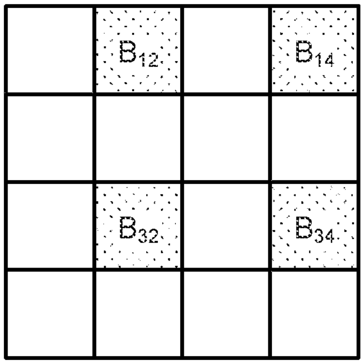
FIG. 7C is a diagram schematically illustrating a signal value of B pixel in an image sensor according to the first embodiment.

The image sensor 53 configured as described above allows the generation of color signals (G, R, and B signals) for the respective G, R, and B pixels in a case of receiving the photographic subject image formed by the optical system 51, as illustrated in FIGS. 7A to 7C.

Referring back to FIG. 2, the description of the configuration of the endoscopic system 1 continues.

The cut filter 54 is arranged on the optical axis L1 between the optical system 51 and the image sensor 53. The cut filter 54 is provided on the light-receiving surface side (incident surface side) of the G pixel provided with the G-filter that is included in the color filter 532 and that allows light in at least the green wavelength band to pass through. The cut filter 54 blocks light in the short wavelength band including the wavelength band of the excitation light and allows light in the longer wavelength band than the wavelength band of the excitation light including narrow-band light to pass through.

Figure 8:
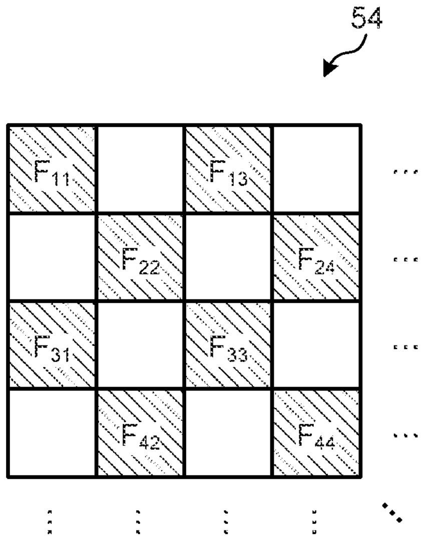
FIG. 8 is a diagram schematically illustrating a configuration of a cut filter according to the first embodiment.

FIG. 8 is a diagram schematically illustrating the configuration of the cut filter 54. As illustrated in FIG. 8, a filter $F_{11}$ that constitutes the cut filter 54 is arranged at the position where a filter $G_{11}$ (see FIG. 5) is arranged, on the side of the light-receiving surface directly above the filter $G_{11}$.

Figure 9:
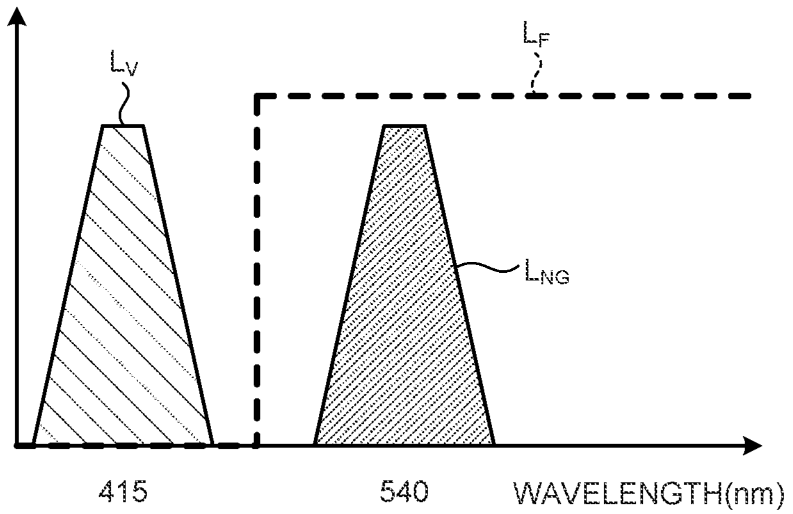
FIG. 9 is a diagram schematically illustrating transmission characteristics of a cut filter according to the first embodiment.

FIG. 9 is a diagram schematically illustrating the transmission characteristics of the cut filter 54. In FIG. 9, the horizontal axis indicates the wavelength (nm), and the vertical axis indicates the transmission characteristics. Furthermore, in FIG. 9, a polygonal line $L_F$ indicates the transmission characteristics of the cut filter 54, a polygonal line $L_{NG}$ indicates the first wavelength characteristics, and a polygonal line $L_V$ indicates the wavelength characteristics of the excitation light.

As illustrated in FIG. 9, the cut filter 54 blocks light in the wavelength band of excitation light and allows light in the wavelength band on the longer wavelength band than the wavelength band of excitation light to pass through. Specifically, the cut filter 54 blocks light in a wavelength band on the short wavelength side of less than the range of 400 nm to 430 nm, which includes the wavelength band of excitation light, and allows light in a wavelength band on the longer wavelength side than the range of 400 nm to 430 nm, which includes the wavelength band of excitation light, to pass through.

Referring back to FIG. 2, the description of the configuration of the endoscopic camera head 5 continues.

The analog-to-digital (A/D) converter 55 performs A/D conversion processing on the analog imaging signal input from the image sensor 53 and outputs the result to the P/S converter 56 under the control of the imaging control unit 58. The A/D converter 55 is implemented employing an A/D conversion circuit or the like.

The parallel-to-serial (P/S) converter 56 performs parallel-to-serial conversion on a digital imaging signal input from the A/D converter 55 and outputs the imaging signal subjected to the parallel-to-serial conversion to the controller 9 via the first transmission cable 6 under the control of the imaging control unit 58. The P/S converter 56 is implemented employing a P/S conversion circuit or the like. Moreover, in the first embodiment, instead of the P/S converter 56, an E/O converter that converts an imaging signal into an optical signal can be provided, outputting the imaging signal to the controller 9 as an optical signal. Alternatively, the imaging signal can be sent to the controller 9 by wireless communication such as Wi-Fi (a registered trademark of the Wi-Fi Alliance).

The imaging recorder 57 records various types of information regarding the endoscopic camera head 5 (e.g., pixel information of the image sensor 53 or characteristics of the cut filter 54). In addition, the imaging recorder 57 records various setting data and control parameters transmitted from the controller 9 via the first transmission cable 6. The imaging recorder 57 includes at least one of a non-volatile memory or a volatile memory.

The imaging control unit 58 controls each operation of the driver 52, the image sensor 53, the A/D converter 55, and the P/S converter 56 on the basis of the setting data received from the controller 9 via the first transmission cable 6. The imaging control unit 58 is implemented employing a timing generator (TG), a processor, and a memory. The processor is a processing device that includes hardware such as a CPU, while the memory is a temporary storage area for the processor.

Configuration of Controller

The configuration of the controller 9 is now described.

The controller 9 includes a serial-to-parallel (S/P) converter 91, an image processing unit 92, an input unit 93, a recorder 94, and a control unit 95.

The S/P converter 91 performs serial-to-parallel conversion on image data received from the endoscopic camera head 5 via the first transmission cable 6 and outputs the result to the image processing unit 92, which is performed under the control of the control unit 95. Moreover, in a case where the endoscopic camera head 5 outputs an imaging signal in the form of an optical signal, an optical-to-electrical (O/E) converter that converts optical signals into electrical signals can be provided in place of the S/P converter 91. In addition, in a case where the endoscopic camera head 5 sends an imaging signal by wireless communication, a communication module capable of receiving a wireless signal can be provided in place of the S/P converter 91.

The image processing unit 92 performs predetermined image processing on the imaging signal in the form of parallel data input from the S/P converter 91 and outputs the result to the display 7, which is performed under the control of the control unit 95. The predetermined image processing herein includes demosaicing, white balancing, gain adjustment, gamma (Y) correction, format conversion processing, and the like. The image processing unit 92 is implemented employing a processor and a memory. The processor is a processing device that includes hardware such as a GPU or FPGA, while the memory is a temporary storage area for the processor. Moreover, in the first embodiment, the image processing unit 92 functions as an assistant device. The image processing unit 92 has a generation unit 921, an identification unit 922, a determination unit 923, and an output unit 924.

The generation unit 921 generates a first image including one or more characteristic regions that need to be excised by a surgical operator and a second image including one or more cauterized regions cauterized by the energy device. Specifically, the generation unit 921 generates the first image on the basis of an imaging signal obtained by capturing reflected light and return light from the living tissue in the case where the living tissue is irradiated with narrow-band light with a narrower wavelength band than white light. More specifically, the generation unit 921 generates the first image, which is a pseudo-color image including one or more characteristic regions (lesion sites) that need to be excised by the surgical operator on the basis of an imaging signal, which is obtained by capturing reflected light and return light from the living tissue in the case where the living tissue is irradiated with the first narrow-band light and the second narrow-band light in the narrow-band imaging observation mode of the endoscopic system 1, which will be described later. In addition, the generation unit 921 generates the second image on the basis of an imaging signal obtained by capturing fluorescence generated by excitation light applied to excite advanced glycation end products produced by subjecting the living tissue to thermal treatment in the thermal treatment imaging observation mode of the endoscopic system 1, which will be described later.

The identification unit 922 calculates a hue H of each pixel in the first image, which is the pseudo-color image generated by the generation unit 921, and identifies a pixel having a brown color (e.g., a hue H of 5 to 35) as a characteristic region (lesion site). The hue H is herein one of the attributes of color (hue, saturation, and brightness) and the aspect of color represented by a numerical value in the range of 0 to 360 using what is called the Munsell color wheel (e.g., red, blue, and yellow). Moreover, the identification unit 922 can determine whether or not each pixel of the first image, which is the pseudo-color image generated by the generation unit 921, has a predetermined luminance (gradation value) or more, identifying the characteristic region (lesion site) by extracting a pixel with a brightness higher than a predetermined value. In addition, the identification unit 922 determines whether or not the luminance value (gradation value) of each pixel of the second image, which is the fluorescence image generated by the generation unit 921, is equal to or greater than a predetermined threshold value, identifying a pixel equal to or greater than a predetermined threshold as a cauterized region.

The determination unit 923 determines whether or not the characteristic region is included in the cauterized region on the basis of the first image and the second image generated by the generation unit 921. Specifically, the determination unit 923 determines whether or not the entire characteristic region is included in the cauterized region on the basis of the first image and the second image generated by the generation unit 921.

The output unit 924 outputs information indicating that there is a characteristic region (lesion site) that still needs to be cauterized in the case where the determination unit 923 determines that the characteristic region (lesion site) is not included in the cauterized region.

The input unit 93 receives inputs for various operations related to the endoscopic system 1 and outputs the received operations to the control unit 95. Examples of the input unit 93 include a mouse, foot switch, keyboard, buttons, switches, touch panel, and the like.

The recorder 94 is implemented employing recording media such as volatile memory, non-volatile memory, solid-state drive (SSD), hard disk drive (HDD), or the like, and memory cards. The recorder 94 is used to record data including various parameters required for the operation of the endoscopic system 1. In addition, the recorder 94 also has a program recording unit 941 that records various programs used for endoscopic system 1 to operate.

The control unit 95 is implemented employing a processor and a memory. The processor is a processing device that includes hardware such as an FPGA or CPU, while the memory is a temporary storage area for the processor. The control unit 95 centrally controls each unit that configures the endoscopic system 1.

Overview of Observation Modes

An overview of observation modes executable by the endoscopic system 1 is now described. Moreover, the description below is given in the order of a narrow-band imaging observation mode, a thermal treatment imaging observation mode, and a normal light imaging observation mode.

Overview of Narrow-Band Imaging Observation Mode

Figure 10:
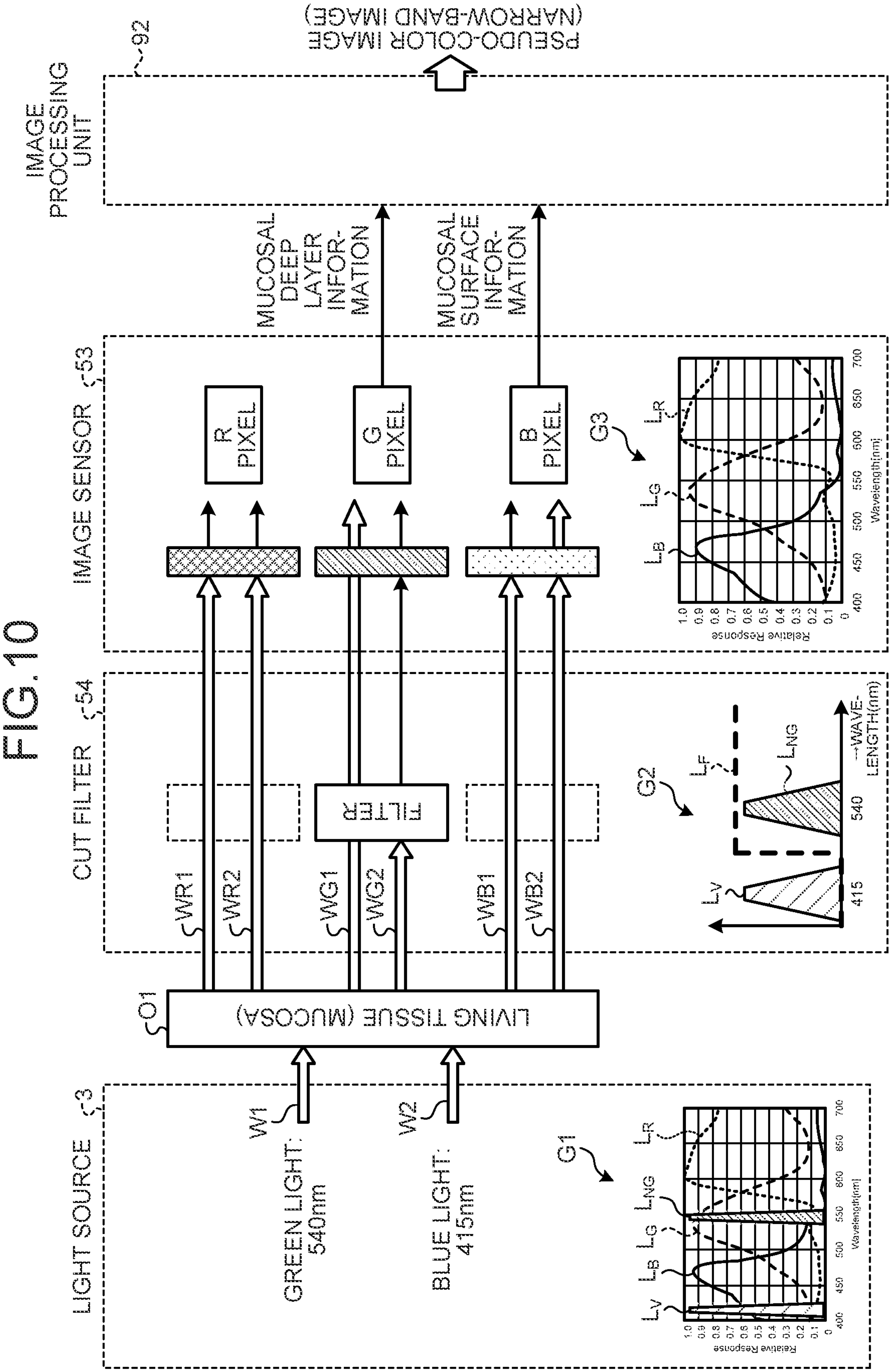
FIG. 10 is a diagram schematically illustrating an image observation principle in a narrow-band imaging observation mode according to the first embodiment.

First, the narrow-band imaging observation mode will be described. FIG. 10 is a diagram schematically illustrating an image observation principle in a narrow-band imaging observation mode.

The narrow-band imaging (NBI) observation mode is an imaging observation technology that enhances the visibility of the capillaries and mucosal surface structure of the mucosal surface of living tissue by using the properties of hemoglobin in blood that strongly absorbs light at a wavelength of around 415 nm. In other words, in the narrow-band imaging observation mode, a subject of living tissue or the like is irradiated with two narrow-banded light beams more likely to be absorbed by hemoglobin in blood. These two narrow-banded light beams are a first narrow-band light beam (with a wavelength band ranging from 530 nm to 550 nm) and a second narrow-band light beam (with a wavelength band ranging from 390 nm to 445 nm). This configuration employing the narrow-band imaging observation mode makes it possible to enhance the visibility of capillaries on the mucosal surface and micro patterns of the mucous membrane, which are difficult to recognize visually with normal light (white light).

Specifically, as illustrated in the graph G1 of FIG. 10, the light source 3 first causes the second light source unit 32 and the third light source unit 33 to emit light under the control of the controller 9, irradiating a living tissue O1 (mucosa) of a subject with a first narrow-band light beam W1 and a second narrow-band light beam W2. In this case, the reflected light and return light beams (simply referred hereinafter to as "reflected light beams WR1, WR2, WG1, WG2, WB1, and WB2") include at least a plurality of components reflected by the living tissue O1 of the subject or the like. A part of the reflected light and return light is blocked by the cut filter 54, and the rest is incident on the image sensor 53. Moreover, the following description is given assuming that the reflected light from the first narrow-band light beam W1 is the reflected light beam WR1, the reflected light beam WG1, and that the reflected light beam WB1 and the reflected light from the second narrow-band light beam W2 is the reflected light beam WR2, the reflected light beam WG2, and the reflected light beam WB2. Moreover, in FIG. 10, the strength of each line component (light quantity or signal value) is represented by thickness.

More specifically, as illustrated by the polygonal line $L_F$ of the graph G2 in FIG. 10, the cut filter 54 blocks the reflected light beam WG2 incident on the G pixel in the short wavelength band including the wavelength band of the second narrow-band light beam W2.

Furthermore, the cut filter 54 allows the reflected light beam WG1 in the wavelength band longer than the wavelength band of the second narrow-band light beam W2, which includes the first narrow-band light beam W1 to pass through. In addition, the reflected light beams (reflected light beams WR1, WR2, WB1, and WB2) obtained by reflecting the first narrow-band light beam W1 and the second narrow-band light beam W2 from the subject are incident on the corresponding R and B pixels.

Subsequently, in FIG. 10, as illustrated in the graph G3 indicating transmission characteristics, the R, G, and B pixels have different transmission characteristics (sensitivity characteristics) from each other.

Specifically, the B pixel has no sensitivity to the reflected light beam WB1 of the first narrow-band light beam W1, so the output value corresponding to the received quantity of the reflected light beam WB1 has a relatively small value. On the other hand, the B pixel has a sensitivity to the reflected light beam WB2 of the second narrow-band light beam W2, so the output value corresponding to the received quantity or intensity of the reflected light beam WB2 has a relatively large value.

The image processing unit 92 then acquires an imaging signal (raw data) from the image sensor 53 of the endoscopic camera head 5 and performs image processing on each of the signal values of the G pixels and B pixels included in the acquired imaging signal to produce a pseudo-color image (narrow-band image). In this case, the signal value of the G pixel includes mucosal deep layer information of the subject. In addition, the signal value of the B pixel includes mucosal surface information of the subject. For this reason, the image processing unit 92 performs image processing such as gain control processing, pixel interpolation processing, and mucosa enhancement processing on each signal value of the G pixels and B pixels included in the imaging signal to generate and output a pseudo-color image to the display 7. The pseudo-color image is herein an image generated using only the signal value of the G pixel and the signal value of the B pixel. In addition, the image processing unit 92 acquires the signal value of the R pixel, but deletes the signal value of the R pixel without using the signal value of the R pixel for generating the pseudo-color image.

As described above, the narrow-band imaging observation mode makes it possible to enhance the visibility of capillaries on the mucosal surface and micro patterns of the mucous membrane, which are difficult to recognize visually with white light (normal light).

Overview of Thermal Treatment Imaging Observation Mode

Figure 11:
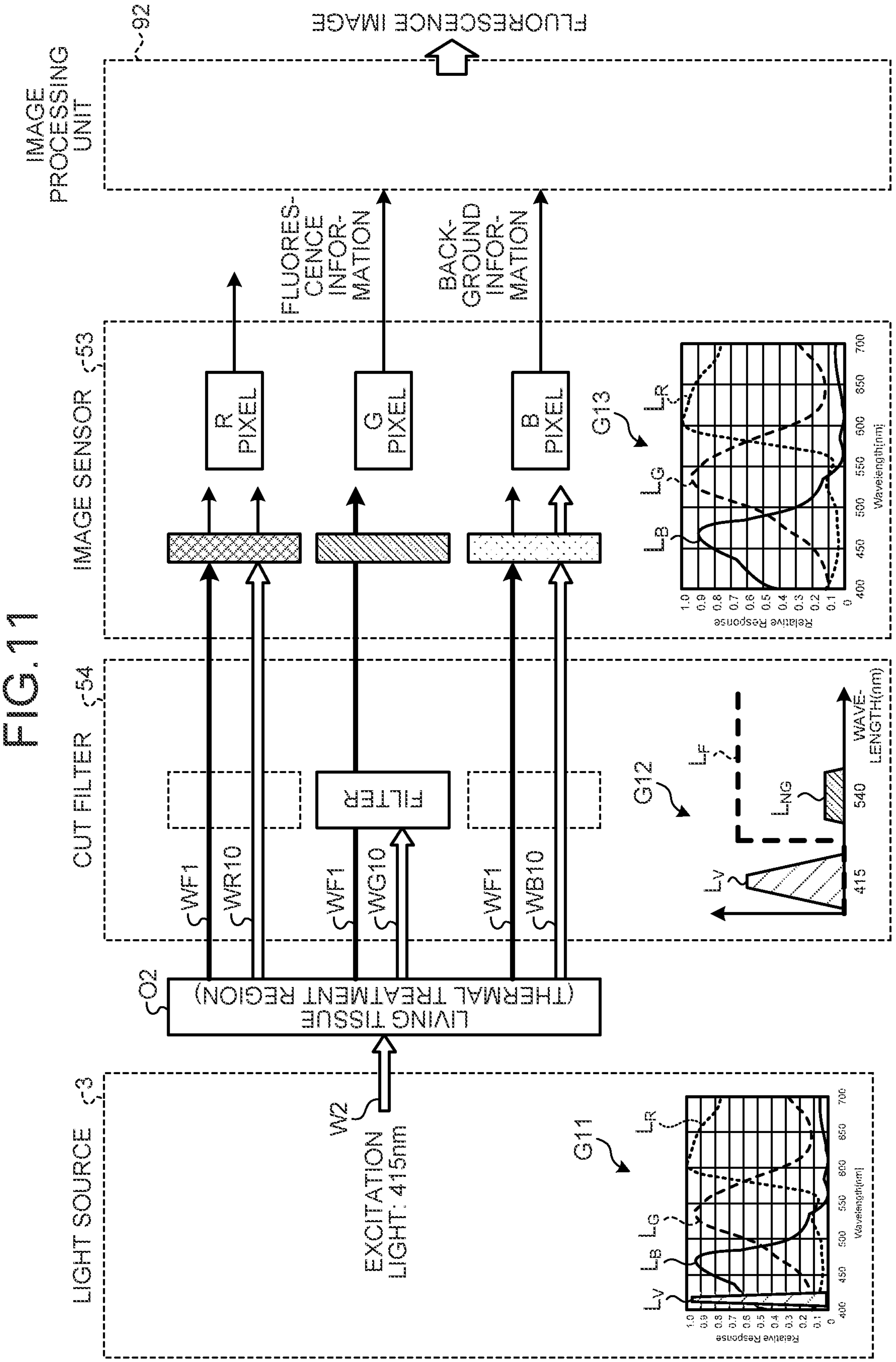
FIG. 11 is a diagram schematically illustrating an image observation principle in a thermal treatment imaging observation mode according to the first embodiment.

Next, the thermal treatment imaging observation mode will be described. FIG. 11 is a diagram schematically illustrating an image observation principle in a thermal treatment imaging observation mode.

In recent years, minimally invasive treatments using an endoscope, laparoscope, or the like have become widely used in the medical field. Examples of minimally invasive treatments using an endoscope, laparoscope, or the like include endoscopic submucosal dissection (ESD), laparoscopy and endoscopy cooperative surgery (LECS), non-exposed endoscopic wall-inversion surgery (NEWS), transurethral resection of bladder tumors (TUR-bt), or the like, which are widely practiced.

In such minimally invasive treatments, a surgical operator, including a surgeon, performs an excision by cauterization, a marking treatment by thermal treatment, or the like on a characteristic region (pathogenic region) having a lesion in living tissue using an energy device treatment instrument that emits energy such as high frequency, ultrasonic wave, microwave, or the like in performing the treatment, which is intended to mark biologically a surgical target region as pretreatment. Furthermore, the surgical operator uses an energy device or the like to perform the treatment such as excision and coagulation of the living tissue of the subject, even in actual treatment.

The actual situation is that the degree of thermal treatment applied to the living tissue by an energy device is checked by the surgical operator relying on naked eye, tactile, and intuition. For this reason, the treatments using an energy device, or the like in the related art is difficult for the surgical operator to check in real time the degree of thermal treatment to be applied during procedures such as surgery, resulting in a medical task requiring a great deal of skill. This situation has led to the desire of the surgical operator or the like for a technique capable of visualizing the cauterized state in the thermally treated region by the thermal treatment in thermally treating the living tissue using the energy device.

Moreover, a glycation reaction (Maillard reaction) occurs in the case where amino acids and reducing sugars are heated. The end products resulting from this Maillard reaction are generally called advanced glycation end products (AGEs). AGEs are known to include a substance having fluorescence characteristics.

In other words, AGEs are produced when the living tissue is thermally treated with an energy device, the amino acids and reducing sugars in the living tissue are heated, and the Maillard reaction occurs. The AGEs produced by this heating enable visualization of the state of the thermal treatment by fluorescence imaging observation. Furthermore, AGEs are known to emit stronger fluorescence than autofluorescent substances originally present in living tissue.

In other words, the thermal treatment imaging observation mode is an imaging observation technique that visualizes the thermally treated region by utilizing the fluorescence characteristics of AGEs produced in living tissue subjected to thermal treatment with an energy device or the like. For this reason, in the thermal treatment imaging observation mode, the living tissue is irradiated with blue light having a wavelength of around 415 nm for exciting AGEs from the light source 3. This configuration allows a thermal treatment image (fluorescence image) obtained by image-capturing the fluorescence (e.g., green light with a wavelength ranging from 490 nm to 625 nm) produced from AGEs to be observed in the thermal treatment imaging observation mode.

Specifically, as illustrated in the graph G11 of FIG. 11, the light source 3 first causes the third light source unit 33 to emit light under the control of the controller 9. Thus, a living tissue O2 (thermal treatment region) of a subject that is thermally treated by an energy device or the like is irradiated with the second narrow-band light beam W2, which is excitation light (with a center wavelength of 415 nm). In this case, as illustrated in the graph G12 of FIG. 11, the reflected light (referred hereinafter to as "reflected light beam WR10, reflected light beam WG10, and reflected light beam WB10") is blocked by the cut filter 54. This reflected light includes at least the component of the second narrow-band light beam W2 reflected by the living tissue O2 (thermal treatment region) and the return light. A part of the components on the longer wavelength side of the reflected light is incident on the image sensor 53. Moreover, in FIG. 11, the strength of each line component (light quantity or signal value) is represented by thickness.

More specifically, as illustrated in the graph G12 of FIG. 11, the cut filter 54 blocks the reflected light beam WG2 in a wavelength band with a short wavelength that includes the wavelength band of the second narrow-band light beam W2, the reflected light beam WG2 being incident on the G pixel. Furthermore, as illustrated in the graph G12 of FIG. 11, the cut filter 54 causes fluorescence WF1 that is auto-luminous by AGEs in the living tissue O2 (thermal treatment region) to be passed through. Thus, the reflected light (reflected light beam WR12 and reflected light beam WB12) and the fluorescence WF1 are incident on each of the R pixel and the B pixel. In addition, the fluorescence WF1 is incident on the G pixel. In this way, in the G pixel, the cut filter 54 is arranged on the light-receiving surface side (incident surface side), so it is possible to prevent the fluorescence component from being buried in the reflected light beam WG2 of the second narrow-band light beam W2, which is the excitation light.

Further, as illustrated by the polygonal line $L_{NG}$ Of the fluorescence characteristics in the graph G12 of FIG. 11, the G pixel has a sensitivity to fluorescence, but the output value is relatively small due to the minute fluorescence response.

The image processing unit 92 then acquires image data (raw data) from the image sensor 53 of the endoscopic camera head 5 and performs image processing on each signal value of the G pixel and B pixel included in the acquired image data to generate a fluorescence image (pseudo-color image). In this case, the signal value of the G pixel includes information regarding fluorescence emitted from the thermal treatment region. In addition, the B pixel includes information regarding the background, which is the living tissue surrounding the thermal treatment region. For this reason, the image processing unit 92 performs image processing such as gain control processing, pixel interpolation processing, and mucosa enhancement processing on the signal values of the G pixel and the B pixel included in the image data to generate a fluorescence image (pseudo fluorescence image). Then, the image processing unit 92 outputs the fluorescence image (pseudo-color image) to the display 7. In this case, the image processing unit 92 performs gain control processing to make the gain for the signal value of the G pixel larger than the gain for the signal value of the G pixel during the normal light imaging observation and to make the gain for the signal value of the B pixel smaller than the gain for the signal value of the B pixel during the normal light imaging observation. Furthermore, the image processing unit 92 performs gain control processing so that the signal value of the G pixel and the signal value of the B pixel are the same (1:1).

As described above, in the thermal treatment imaging observation mode, it is possible to easily observe the living tissue O2 (thermal treatment region) to be subjected to thermal treatment by an energy device or the like.

Overview of Normal Light Imaging Observation Mode

Figure 12:
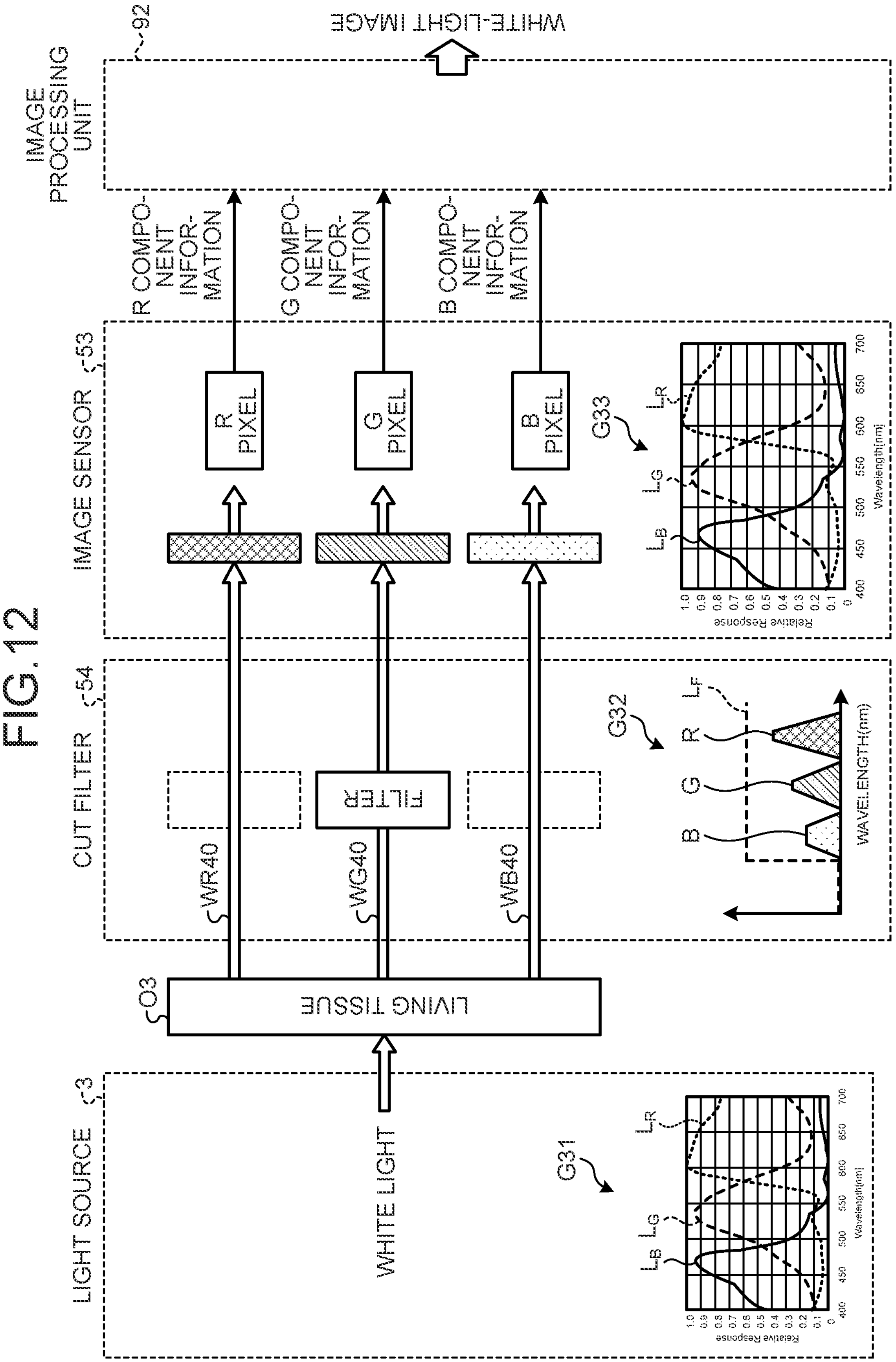
FIG. 12 is a diagram schematically illustrating an image observation principle in a normal light imaging observation mode according to the first embodiment.

Next, the normal light imaging observation mode will be described. FIG. 12 is a diagram schematically illustrating an image observation principle in a normal light imaging observation mode.

As illustrated in FIG. 12, the light source 3 first causes the first light source unit 31 to emit light to irradiate a living tissue O3 of a subject with a white light beam W3 under the control of the controller 9. In this case, a part of the reflected light and return light reflected by the living tissue (hereinafter simply referred to as "reflected light beam WR40, reflected light beam WG40, and reflected light beam WB40") is blocked by the cut filter 54, and the rest is incident on the image sensor 53. Specifically, as illustrated in FIG. 12, the cut filter 54 blocks the reflected light (reflected light beam WG30) in a wavelength band with a short wavelength that includes the wavelength band of the second narrow-band light beam W2, the reflected light being incident on the G pixel. Thus, as illustrated in FIG. 12, the component of light in the blue wavelength band incident on the G pixel is smaller than the case where the cut filter 54 is not arranged.

Subsequently, the image processing unit 92 acquires image data (raw data) from the image sensor 53 of the endoscopic camera head 5 and performs image processing on the signal values of each of the R, G, and B pixels included in the acquired image data to generate a white-light image. In this case, the image processing unit 92 performs white balance adjustment processing that adjusts the white balance so that the ratio of the red, green, and blue components is constant because the blue component included in the image data is smaller than that in the white-light imaging observation in the related art.

Thus, in the normal light imaging observation mode, it is possible to observe a natural white-light image (observation image) even in the case where the cut filter 54 is arranged on the light-receiving surface side of the G pixel.

Procedure for Transurethral Resection of Bladder Tumors

The procedure for the transurethral resection of bladder tumors performed by a surgical operator is described. Moreover, the conventional transurethral resection of bladder tumors is first described, followed by a description of the novel transurethral resection of bladder tumors using the endoscopic system 1 of the present disclosure is given. The conventional transurethral resection of bladder tumors uses photodynamic diagnosis (PDD) in which treatment is conducted while observing both the tumor and treatment sites by administering a photosensitizer, such as conventional 5-aminolevulinic acid (hereinafter referred to as "5-ALA"), into the body of the subject, and then observing the fluorescence produced by irradiating protoporphyrin IX (hereinafter referred to as "PPIX") accumulated in the tumor with excitation light.

Procedure for Conventional Transurethral Resection of Bladder Tumors Using PDD

Figure 13:
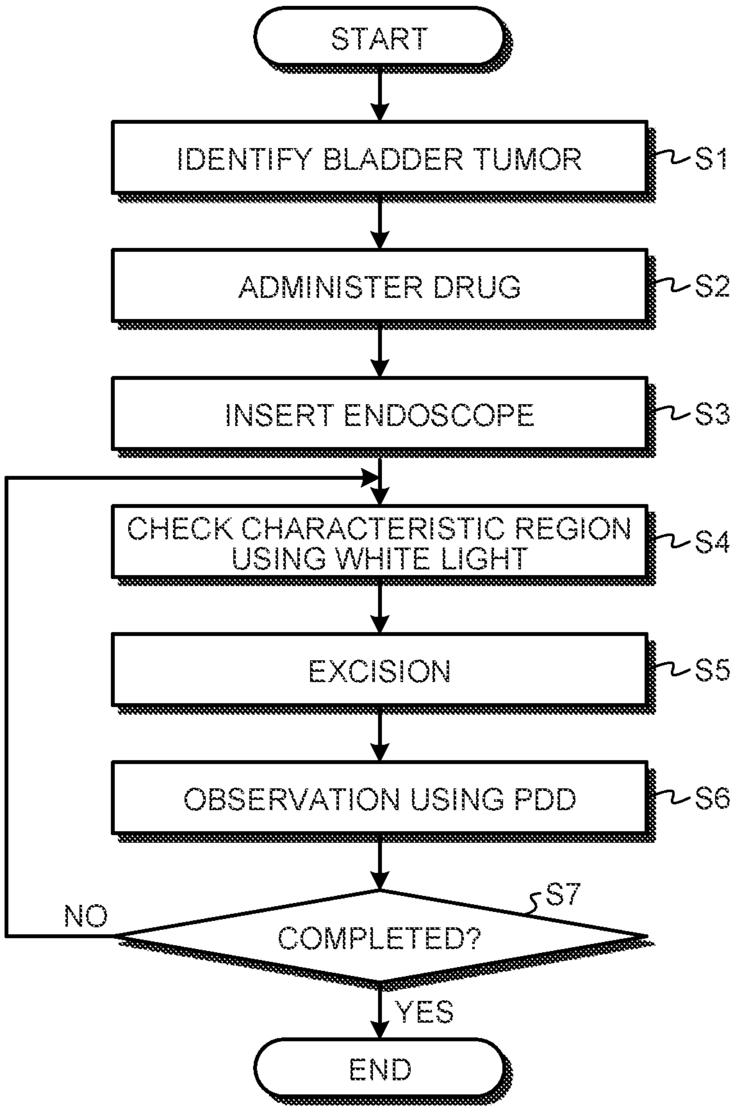
FIG. 13 is a flowchart illustrating a procedure for the PDD-assisted transurethral resection of bladder tumors in the related art.

The procedure for the conventional transurethral resection of bladder tumors using PDD is now described. FIG. 13 is a flowchart illustrating the procedure for the conventional transurethral resection of bladder tumors using PDD.

As illustrated in FIG. 13, a surgical operator first identifies a bladder tumor in a subject of a patient or the like (Step S1). Specifically, the surgical operator checks whether or not a tumor is developed in the subject using a tumor marker or the like obtained by a urine examination and performs an endoscopic (cystoscopy) examination. In this case, the surgical operator uses an endoscope to perform a biopsy to collect urine cells from the subject. In addition, the surgical operator identifies the bladder tumor of the subject by performing various examinations such as abdominal ultrasonography, CT examination, and MRI examination on the subject. Specifically, the surgical operator makes a definitive diagnosis with a microscope on the urine cells collected by biopsy, determines the three likenesses of the subject's T (depth of bladder cancer), N (presence or absence of lymph node metastasis), and M (presence or absence of distant metastasis such as lung, liver, and bone) on the basis of various examination, and identifies the stage of the bladder tumor in the subject.

Subsequently, if a bladder tumor is detected in the subject, the surgical operator identifies the bladder tumor and then administers 5-ALA to the subject (Step S2). Specifically, the surgical operator causes the subject to take a drug containing 5-ALA before surgery.

Then, the surgical operator inserts the endoscope through the urethra of the subject (Step S3) and checks the specific region (lesion site) including the tumor position in the bladder using the white light of the endoscope (Step S4). In this case, the surgical operator checks the rough specific region including the tumor position while checking the observation image displayed on the display.

Subsequently, the surgical operator cauterizes and excises the lesion site including a lesion of the subject with an energy device or the like through the endoscope while checking a fluorescence image P1 displayed on the display (Step S5).

Figure 14:
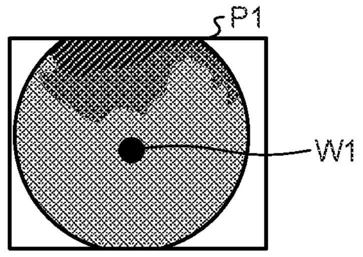
FIG. 14 is a diagram illustrating an example of a fluorescence image displayed during the PDD-assisted transurethral resection of bladder tumors in the related art.

Then, the surgical operator switches the endoscope to a PDD mode and causes the endoscope to apply the second narrow-band light to perform observation using PDD (Step S6). In this case, as illustrated in FIG. 14, the surgical operator checks the fluorescence image P1 obtained by the PDD displayed on the display, detecting the fluorescence region W1 emitting red light as a specific region (lesion site) including a lesion such as a tumor.

Subsequently, the surgical operator observes the fluorescence image P1 displayed on the display to determine whether or not the excision of the tumor is completed (Step S7). If the excision for all the targeted tumors is completed (Step S7: Yes), the surgical operator ends the procedure. Specifically, while observing the fluorescence image P1 displayed on the display, the surgical operator determines whether or not the entire fluorescence region W1 of the fluorescence image P1 is excised. If the entire fluorescence region W1 is excised, then the excision of the specific region (lesion site) including the lesion such as a tumor is determined to be completed, and the procedure ends. On the other hand, if the excision of all the tumors is not completed (Step S7: No), the surgical operator returns to the previous Step S4 and continues the procedure until the fluorescence region W1 is cauterized using an energy device or the like while alternately switching the endoscope imaging observation mode between the white-light observation image and the PDD-assisted fluorescence image P1.

Thus, the procedure for conventional transurethral resection of bladder tumors using PDD requires the administration of 5-ALA to the subject.

Figure 15:
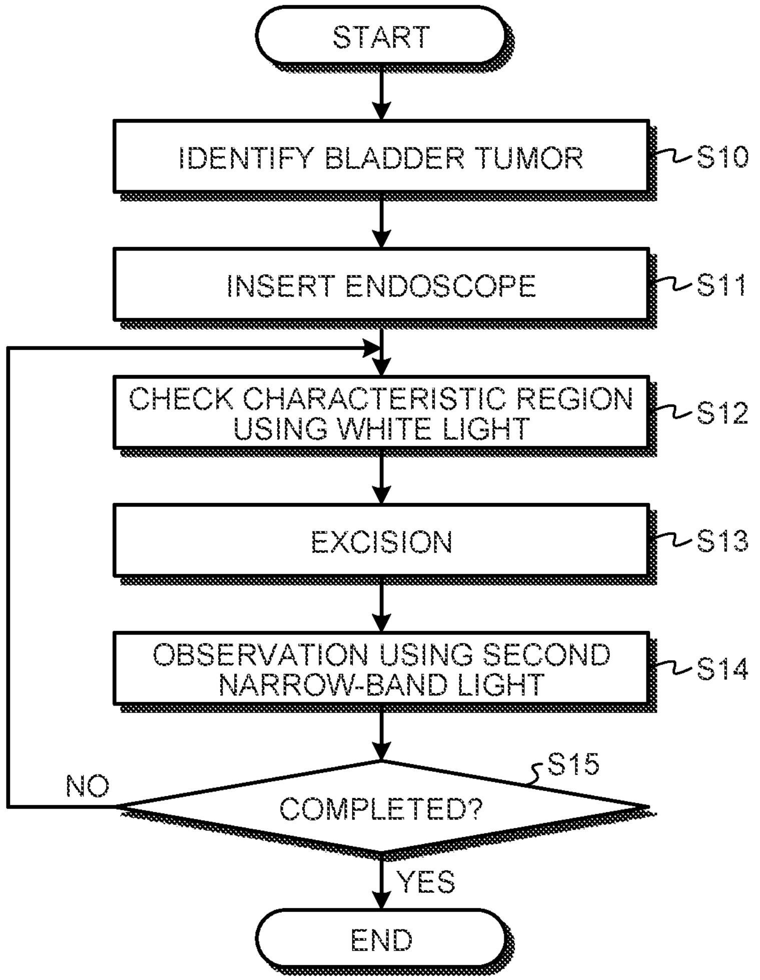
FIG. 15 is a flowchart of a procedure for the transurethral resection of bladder tumors using the endoscopic system according to the first embodiment.

Procedure for Transurethral Resection of Bladder Tumors According to Present Disclosure The procedure for the transurethral resection of bladder tumors performed using the endoscopic system 1 according to the present disclosure is now described. FIG. 15 is a flowchart of a procedure for the transurethral resection of bladder tumors using the endoscopic system 1 according to the present disclosure.

As illustrated in FIG. 15, a surgical operator first identifies a bladder tumor in a subject of a patient or the like (Step S10). Specifically, the surgical operator identifies the bladder tumor of the subject by the same method as the transurethral resection of bladder tumors using PDD described above.

Figure 16:
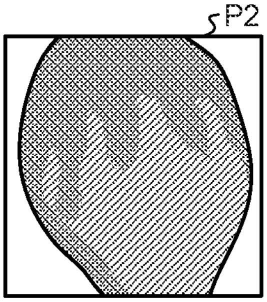
FIG. 16 is a diagram illustrating an exemplary white-light image displayed during the transurethral resection of bladder tumors using the endoscopic system according to the first embodiment.

Subsequently, the surgical operator inserts the insertion portion 2 (rigid endoscope) into the urethra of the subject (Step S11), causes the light source 3 to irradiate the inside of the subject with white light, and confirms a characteristic region (lesion site) including the tumor position while observing the observation image displayed by the display 7 (Step S12). Specifically, as illustrated in FIG. 16, the characteristic region (lesion site) including the tumor position is confirmed while observing the white-light image P2 displayed on the display 7.

Thereafter, the surgical operator cauterizes and excises the characteristic region (lesion site) including a lesion such as a tumor of the subject with an energy device or the like through the insertion portion 2 while checking a white-light image P2 displayed on the display 7 (Step S13). Specifically, as illustrated in FIG. 16, the surgical operator cauterizes and excises the characteristic region (lesion site) with an energy device or the like while checking the white-light image P2 displayed on the display 7.

Thereafter, the surgical operator causes the light source 3 to irradiate the inside of the subject with the second narrow-band light (excitation light), which is the excitation light, and observes the fluorescence image displayed by the display 7 (Step S14).

Figure 17:
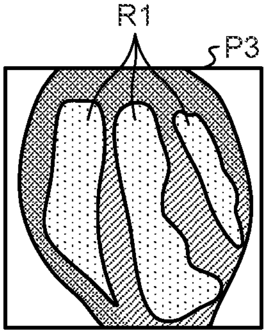
FIG. 17 is a diagram illustrating an exemplary fluorescence image displayed during the transurethral resection of bladder tumors using the endoscopic system according to the first embodiment.

Subsequently, the surgical operator observes the fluorescence image displayed by the display 7 to determine whether or not the excision of the characteristic region (lesion site) including the tumor position is completed (Step S15). If the excision for the characteristic region (lesion site) including the tumor position is completed (Step S15: Yes), the surgical operator ends the procedure. Specifically, as illustrated in FIG. 17, the surgical operator observes the fluorescence image P3 displayed by the display 7 and observes a cauterized region R10 that has been cauterized and excised with an energy device or the like to determine whether or not the excision of the characteristic region (lesion site) including the tumor position is completed. If the excision for the characteristic region (lesion site) including the tumor position is completed, the surgical operator ends the procedure. On the other hand, if the excision for the characteristic region (lesion site) including the tumor position is not completed (Step S15: No), the process returns to Step S12, and the surgical operator cauterizes and excises the characteristic region (lesion site) including the tumor position while alternately switching the observation mode of the endoscopic system 1 between observations of the white-light image P2 displayed by the display 7 by causing the light source 3 to irradiate white light and the fluorescence image P3 displayed by the display 7 by causing the light source 3 to irradiate the inside of the subject with second narrow-band light (excitation light) as excitation light. In this case, the display 7 displays information indicating that there is a lesion site (characteristic region) including a tumor position that has not yet been cauterized.

As described above, according to the transurethral resection of bladder tumors using the endoscopic system 1 of the present disclosure, the tumor of the subject can be excised without administering 5-ALA to the subject, and the characteristic region (lesion site) including the tumor position and the cauterized region can be easily grasped, so that it is possible to prevent the tumor from being left unremoved.

Processing of Endoscopic System

Figure 18:
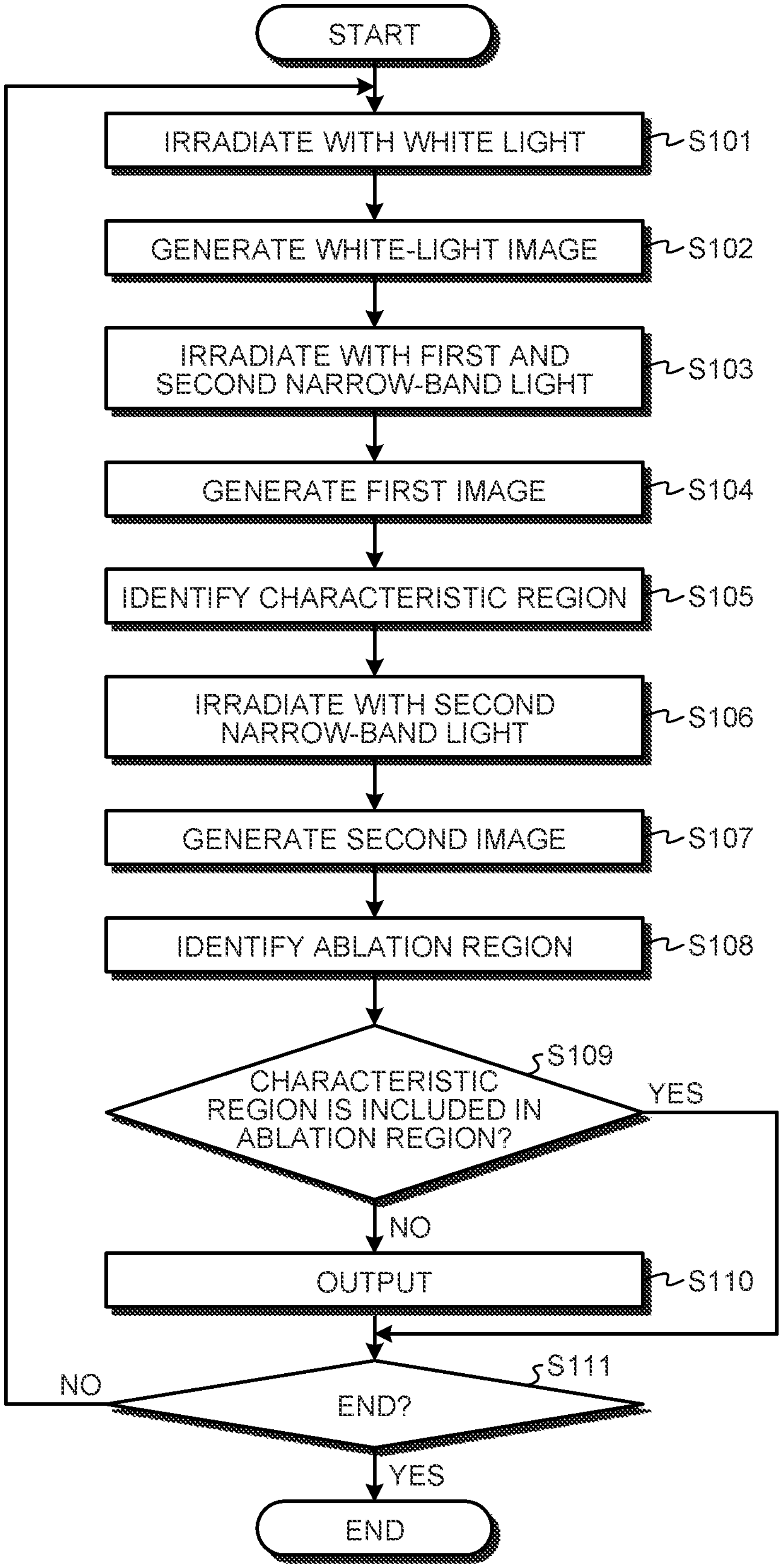
FIG. 18 is a flowchart illustrating an overview of processing executed by the endoscopic system 1 according to the first embodiment.

Next, processing executed by the endoscopic system 1 will be described. FIG. 18 is a flowchart illustrating an overview of processing executed by the endoscopic system 1.

As illustrated in FIG. 18, the control unit 95 controls the light source control unit 34 to cause the first light source unit 31 to irradiate the subject with white light (Step S101).

Subsequently, the generation unit 921 acquires an imaging signal from the image sensor 53 of the endoscopic camera head 5 to generate a white-light image (Step S102). In this case, the output unit 924 causes the display 7 to display the white-light image generated by the generation unit 921.

Thereafter, the control unit 95 controls the light source control unit 34 to cause the second light source unit 32 and the third light source unit 33 to irradiate the photographic subject with the first and second narrow-band light (Step S103).

Subsequently, the generation unit 921 acquires an imaging signal from the image sensor 53 of the endoscopic camera head 5 to generate the first image that is a pseudo-color image (Step S104).

Figure 19:
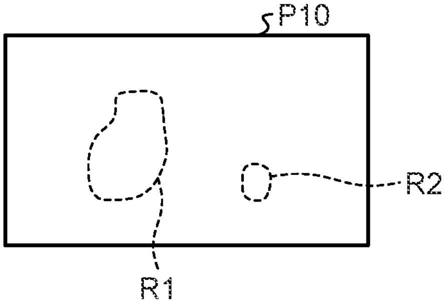
FIG. 19 is a diagram illustrating an exemplary pseudocolor image.

Thereafter, the identification unit 922 identifies the characteristic region (lesion site) from the first image generated by the generation unit 921 (Step S105). Specifies, the identification unit 922 calculates a hue H of each pixel in the first image, which is the pseudo-color image generated by the generation unit 921, and identifies a pixel having a brown color (e.g., a hue H of 5 to 35) as a characteristic region (lesion site). For example, as illustrated in FIG. 19, the identification unit 922 calculates a hue H of each pixel in the first image P10, and identifies a pixel having a brown color (e.g., a hue H of 5 to 35) as a characteristic region (lesion site), for example, characteristic regions R1 and R2.

Subsequently, the control unit 95 controls the light source control unit 34 to cause the third light source unit 33 to irradiate the subject with the second narrow-band light, which is the excitation light (Step S106).

Thereafter, the generation unit 921 acquires an imaging signal from the image sensor 53 of the endoscopic camera head 5 to generate the second image (Step S107).

Figure 20:
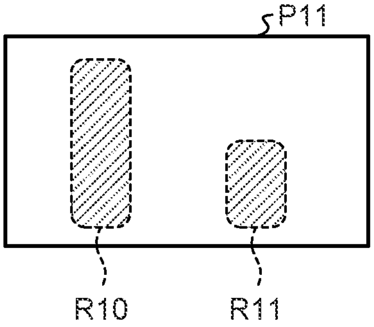
FIG. 20 is a diagram illustrating an exemplary fluorescence image.

Thereafter, the identification unit 922 identifies the cauterized region from the second image (Step S108). Specifically, the identification unit 922 determines whether or not each pixel of the second image has predetermined luminance or more, and extracts pixels having the predetermined luminance or more to identify the cauterized region. Specifically, as illustrated in FIG. 20, the identification unit 922 determines whether or not each pixel of the second image P11 has predetermined luminance or more, and extracts pixels having the predetermined luminance or more to identify the cauterized regions R10 and R11.

Figure 21:
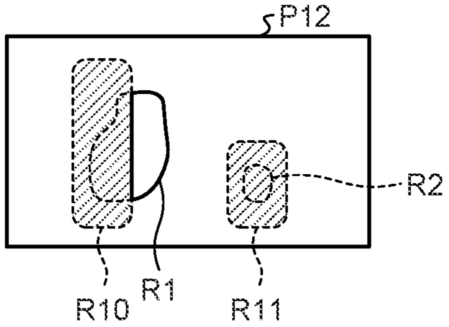
FIG. 21 is a diagram schematically illustrating how a determination unit according to the first embodiment makes determinations.

Subsequently, the determination unit 923 determines whether or not the characteristic region is included in the cauterized region (Step S109). Specifically, as illustrated in FIG. 21, the determination unit 923 determines whether or not the characteristic regions R1 and R2 are included in the cauterized regions R10 and R11 by superimposing the characteristic regions R1 and R2 extracted from the first image P10 by the identification unit 922 and the cauterized regions R10 and R11 extracted from the second image P11. For example, in the case illustrated in FIG. 21, since a part of the characteristic region R1 is out of the cauterized regions R10 and R11, the determination unit 923 determines that there is a characteristic region that has not yet been cauterized, and determines that the characteristic region is not included in the cauterized region. If the determination unit 923 determines that the characteristic region is included in the cauterized region (Step S109: Yes), the endoscopic system 1 proceeds to Step S111 described later. On the contrary, if the determination unit 923 determines that the characteristic region is not included in the cauterized region (Step S109: No), the endoscopic system 1 proceeds to Step S110 described later.

In Step S110, the output unit 924 notifies the display 7 by outputting information indicating that there is a characteristic region (lesion site) that has not yet been cauterized. As a result, the surgical operator can grasp that there is a region that need to be cauterized by an energy device or the like with respect to the characteristic region (lesion site) of the subject, and thus, it is possible to easily grasp the characteristic region (lesion site) being left unremoved.

Subsequently, when the end signal for ending the observation of the subject is input via the input unit 93 (Step S111: Yes), the endoscopic system 1 ends the present processing. On the other hand, when the end signal for ending the observation of the subject is not input via the input unit 93 (Step S111: No), the endoscopic system 1 returns to Step S101 described above.

According to the first embodiment described above, the output unit 924 notifies the display 7 by outputting information indicating that there is a characteristic region (lesion site) that still needs to be cauterized to in the case where the determination unit 923 determines that the characteristic region is not included in the cauterized region. Therefore, the surgical operator can easily grasp the characteristic region (lesion site) being left unremoved.

Furthermore, according to the first embodiment, the generation unit 921 acquires the imaging signal from the image sensor 53 of the endoscopic camera head 5, that is, the imaging signal generated by capturing the reflected light and the return light from the living tissue at the time of irradiating the living tissue with the first and second narrow-band light having a narrower wavelength band than the white light, thereby generating the first image that is the pseudo-color image. Therefore, it is possible to generate the first image including one or more characteristic regions (lesion sites) that need to be excised by a surgical operator.

In addition, according to the first embodiment, the generation unit 921 generates the second image on the basis of an imaging signal obtained by capturing fluorescence generated by excitation light applied to excite advanced glycation end products produced by subjecting the living tissue to thermal treatment, therefore, the second image including one or more cauterized regions cauterized by the energy device.

Second Embodiment

Next, a second embodiment will be described. In the first embodiment described above, the characteristic region (lesion site) is extracted on the basis of the pseudo-color image corresponding to the imaging signal generated by irradiating the subject with the first narrow-band light and capturing the reflected light and the return light from the subject, but in the second embodiment, the characteristic region is identified from the white-light image obtained by capturing the living tissue using the learned model learned using the teacher data in which the plurality of biological images of the subject and the information to which the annotation of the characteristic region (lesion site) included in the plurality of biological images is applied are associated with each other. In the following description, the same components as those of the endoscopic system 1 according to the first embodiment described above are denoted by the same reference numerals, and a detailed description thereof will be omitted.

Functional Configuration of Main Components of Endoscopic System

Figure 22:
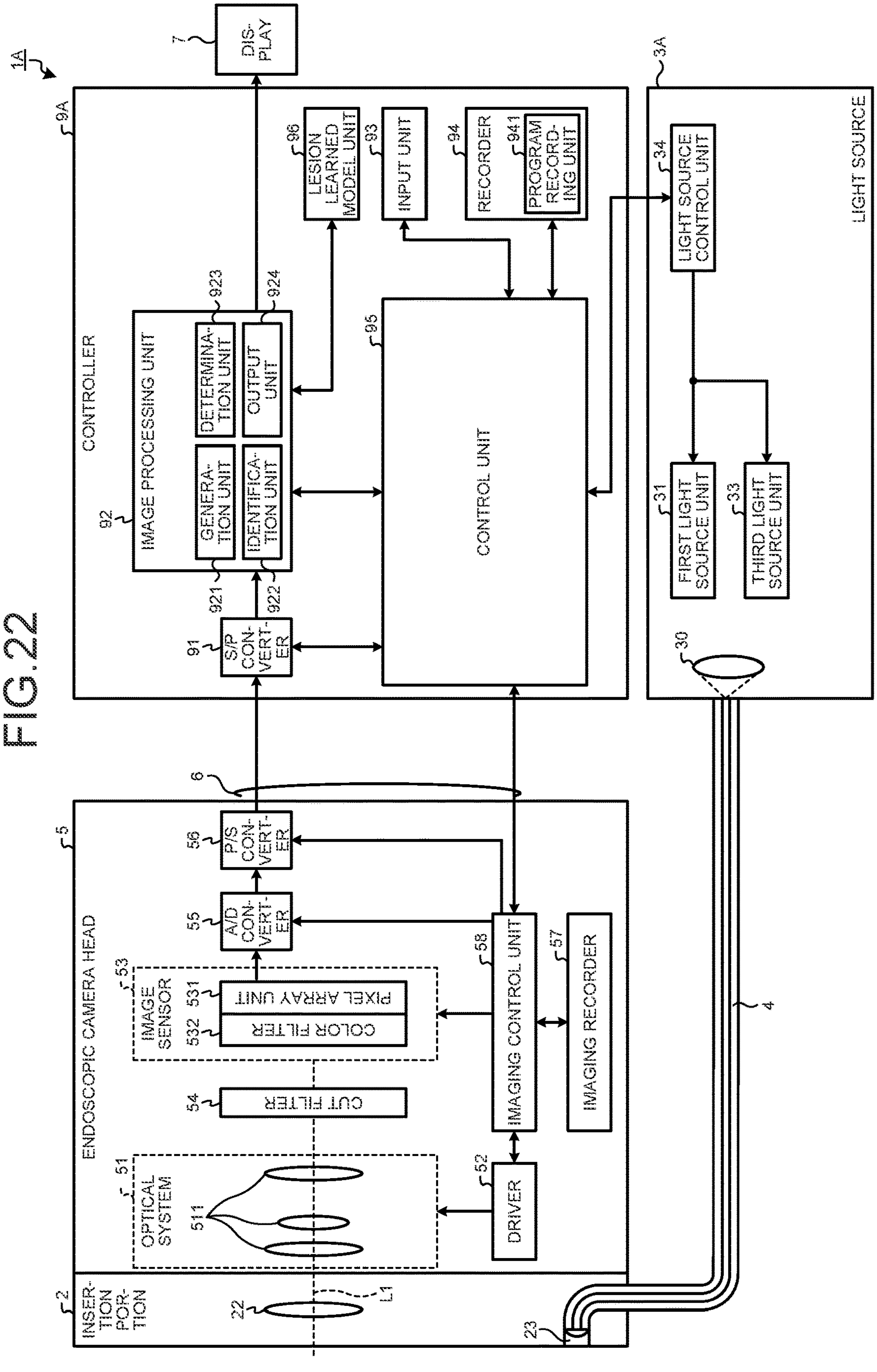
FIG. 22 is a block diagram illustrating a functional configuration of main components of the endoscopic system according to a second embodiment.

FIG. 22 is a block diagram illustrating a functional configuration of main components of the endoscopic system according to the second embodiment. An endoscopic system 1A illustrated in FIG. 22 includes a light source 3A and a controller 9A instead of the light source 3 and the controller 9 of the endoscopic system 1 according to the first embodiment described above.

Configuration of Light Source

First, the configuration of the light source 3A is described. In the light source 3A, the second light source unit 32 capable of emitting the first narrow-band light from the light source 3A according to the above-described first embodiment is omitted.

Configuration of Controller

The configuration of the controller 9A is now described. The controller 9A further includes a lesion learned model unit 96 in addition to the configuration of the controller 9 according to the first embodiment described above.

The lesion learned model unit 96 records a lesion learned model for identifying a characteristic region (lesion site) included in the white-light image.

Specifically, the lesion learned model unit 96 records a learning result learned using teacher data in which a plurality biological images of a subject are associated with information to which annotation of a characteristic region (lesion site) included in the plurality of biological images is applied. The lesion learned model unit 96 inputs an imaging signal generated by capturing reflected light when white light is emitted to a living tissue or return light from the living tissue as input data, and outputs a position of a lesion site in a captured image corresponding to the imaging signal as output data. Here, the lesion learned model includes a neural network in which each layer has one or a plurality of nodes. Furthermore, the type of machine learning is not particularly limited, but for example, it is sufficient that teaching data and learning data in which a plurality of biological images of subjects are associated with information to which annotation of a characteristic region (lesion site) included in the plurality of biological images are applied are prepared, and the teaching data and the learning data are input to a calculation model based on a multilayer neural network to perform learning.

Furthermore, as a machine learning method, for example, a method based on a deep neural network (DNN) of a multilayer neural network such as a convolutional neural network (CNN) or a 3D-CNN is used. Furthermore, as a machine learning method, a method based on a recurrent neural network (RNN), a long short-term memory unit (LSTM) obtained by extending the RNN, or the like may be used.

Processing of Endoscopic System

Figure 23:
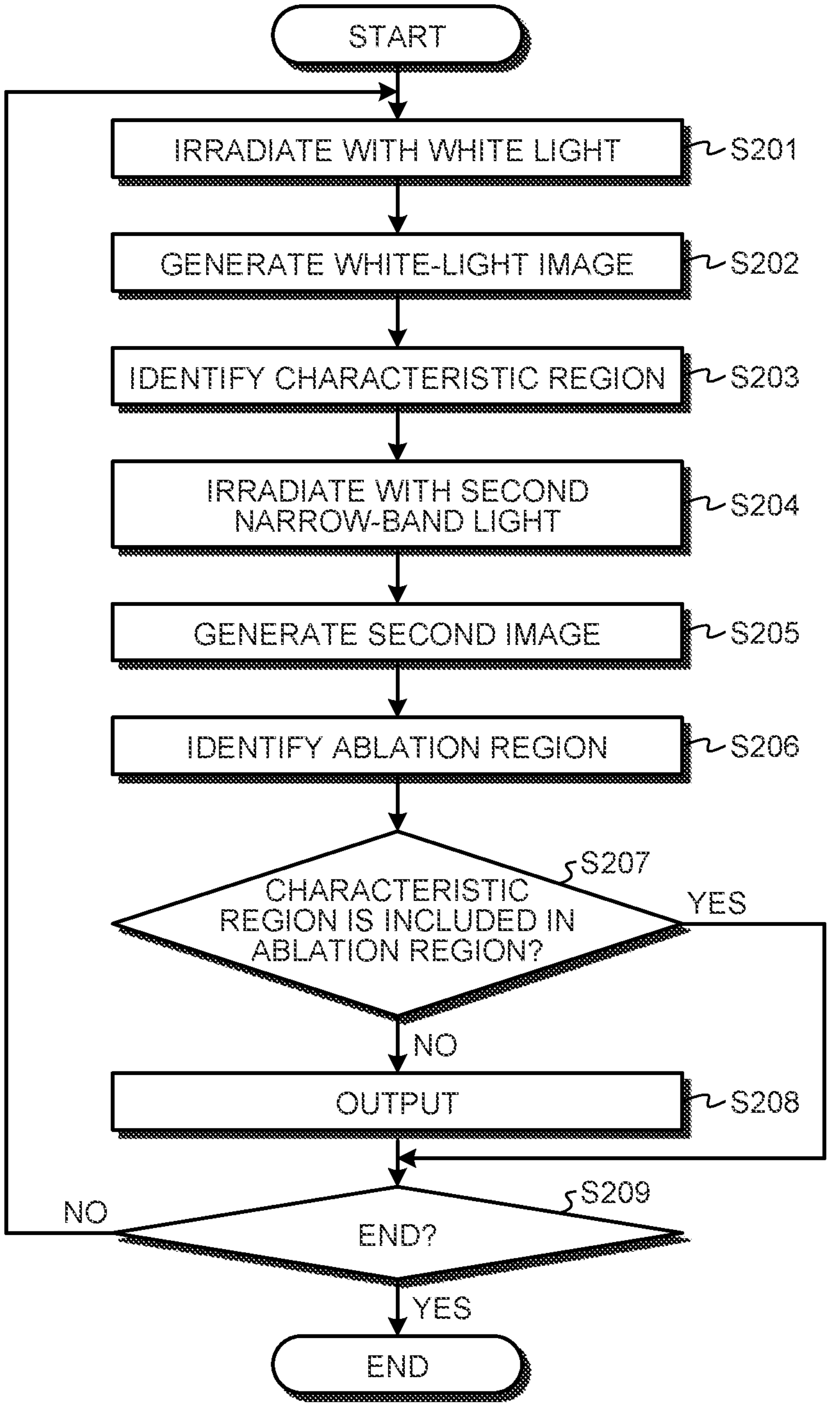
FIG. 23 is a flowchart illustrating an overview of processing executed by the endoscopic system according to the second embodiment.

Next, processing executed by the endoscopic system 1A will be described. FIG. 23 is a flowchart illustrating an overview of processing executed by the endoscopic system 1A. In FIG. 23, Steps S201 and S202 correspond to Steps S101 and S102 in FIG. 18 described above, respectively. In Step S203, the identification unit 922 identifies a characteristic region (lesion site) from the white-light image on the basis of the learned model recorded by the lesion learned model unit 96 and the white-light image generated by the generation unit 921. Specifically, the identification unit 922 inputs the white-light image generated by the generation unit 921 to the lesion learned model unit 96 as input data, and identifies a characteristic region (lesion site) from the white-light image on the basis of the position of the characteristic region output from the lesion learned model unit 96 as output data.

Steps S204 and S209 correspond to Steps S106 and S111 in FIG. 18 described above, respectively. After Step S209, the endoscopic system 1A ends the present processing.

According to the second embodiment described above, similarly to the first embodiment described above, the surgical operator can easily grasp the characteristic region (lesion site) being left unremoved.

Third Embodiment

Next, a third embodiment will be described. In the third embodiment, the surgical operator sets the characteristic region by operating the input unit 93 while observing the white-light image displayed on the display 7 to apply the annotation to the characteristic region (tumor region) appearing in the white-light image. In the following description, the same components as those of the endoscopic system 1 according to the second embodiment described above are denoted by the same reference numerals, and a detailed description thereof will be omitted.

Functional Configuration of Main Components of Endoscopic System

Figure 24:
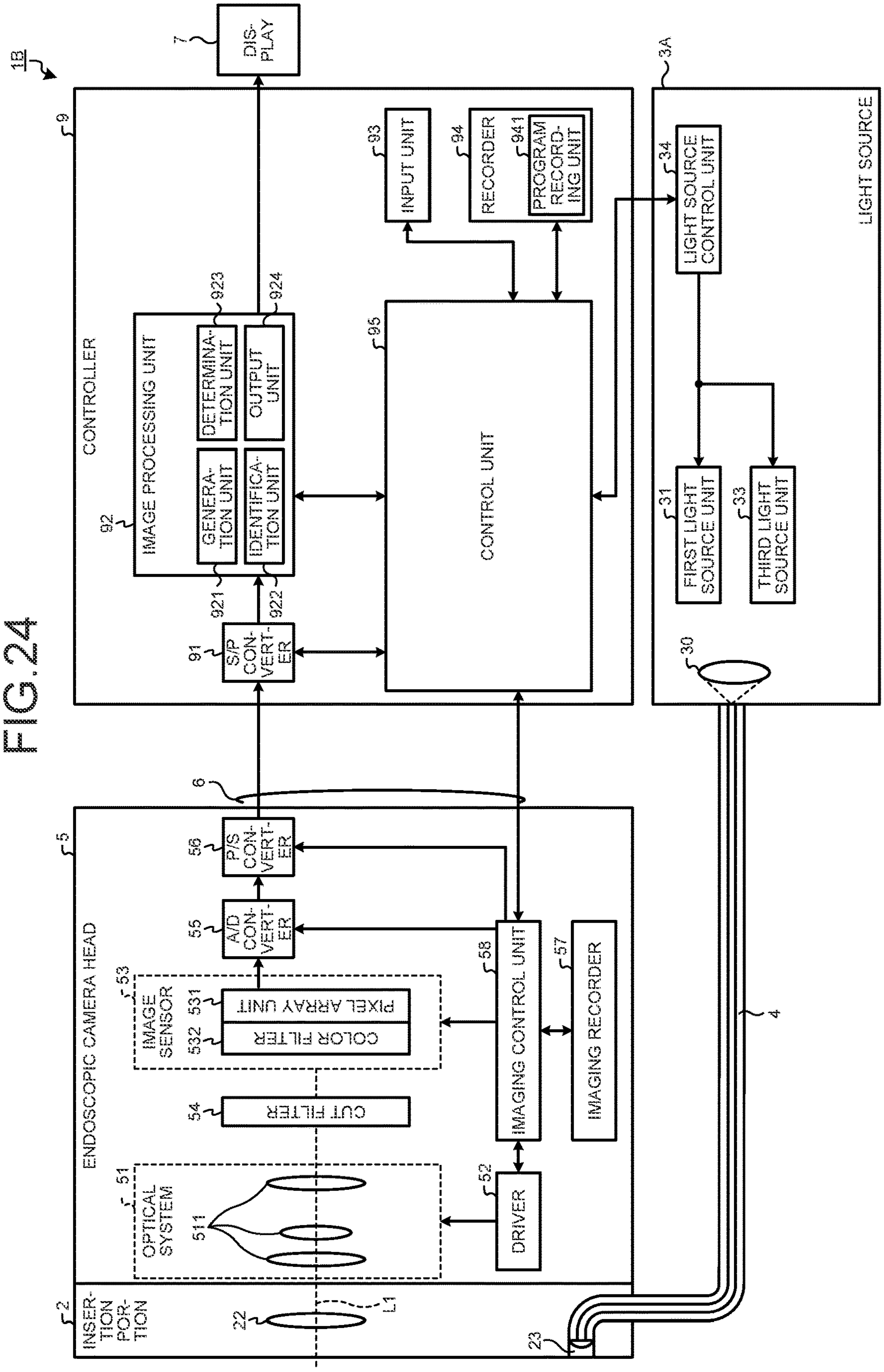
FIG. 24 is a block diagram illustrating a functional configuration of main components of the endoscopic system according to a third embodiment.

FIG. 24 is a block diagram illustrating a functional configuration of main components of the endoscopic system according to the third embodiment. An endoscopic system 1B illustrated in FIG. 24 includes a light source 3A according to the second embodiment described above instead of the light source 3 of the endoscopic system 1 according to the first embodiment described above.

Processing of Endoscopic System

Figure 25:
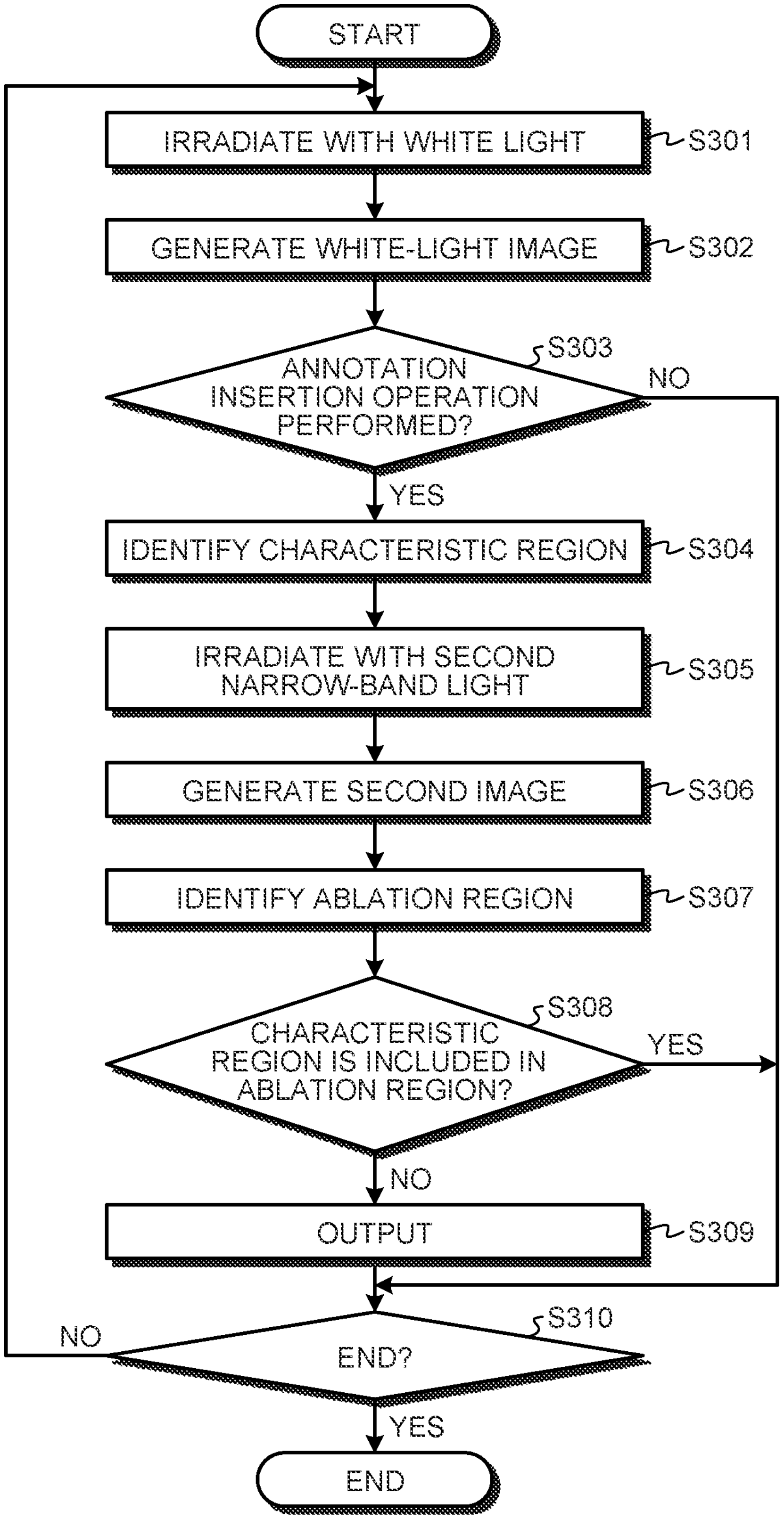
FIG. 25 is a flowchart illustrating an overview of processing executed by the endoscopic system according to the third embodiment.

Next, processing executed by the endoscopic system 1B will be described. FIG. 25 is a flowchart illustrating an overview of processing executed by the endoscopic system 1B. In FIG. 25, Steps S301 and S302 correspond to Steps S101 and S102 in FIG. 18 described above, respectively.

In Step S303, in a case where the surgical operator performs the annotation insertion operation on the white-light image via the input unit 93 (Step S303: Yes), the endoscopic system 1B proceeds to Step S304 described later. On the contrary, in a case where the surgical operator does not perform the annotation insertion operation on the white-light image via the input unit 93 (Step S303: No), the endoscopic system 1B proceeds to Step S311 described later.

In Step S304, the identification unit 922 identifies a region in the white-light image designated according to the annotation insertion operation input from the input unit 93 as a specific region (lesion site). After Step S304, the endoscopic system 1 proceeds to Step S305 described later.

Steps S305 and S310 correspond to Steps S106 and S111 in FIG. 18 described above, respectively. After Step S310, the endoscopic system 1B ends the present processing.

According to the second embodiment described above, similarly to the first embodiment described above, the surgical operator can easily grasp the characteristic region (lesion site) being left unremoved.

Fourth Embodiment

Next, a fourth embodiment will be described. In the above-described first to third embodiments, the endoscopic system includes a rigid endoscope, but in the fourth embodiment, an endoscopic system including a flexible endoscope will be described. Hereinafter, an endoscopic system according to the fourth embodiment will be described. In the fourth embodiment, the same components as those of the endoscopic system 1 according to the first embodiment described above are denoted by the same reference numerals, and a detailed description thereof will be omitted.

Configuration of Endoscopic System

Figure 26:
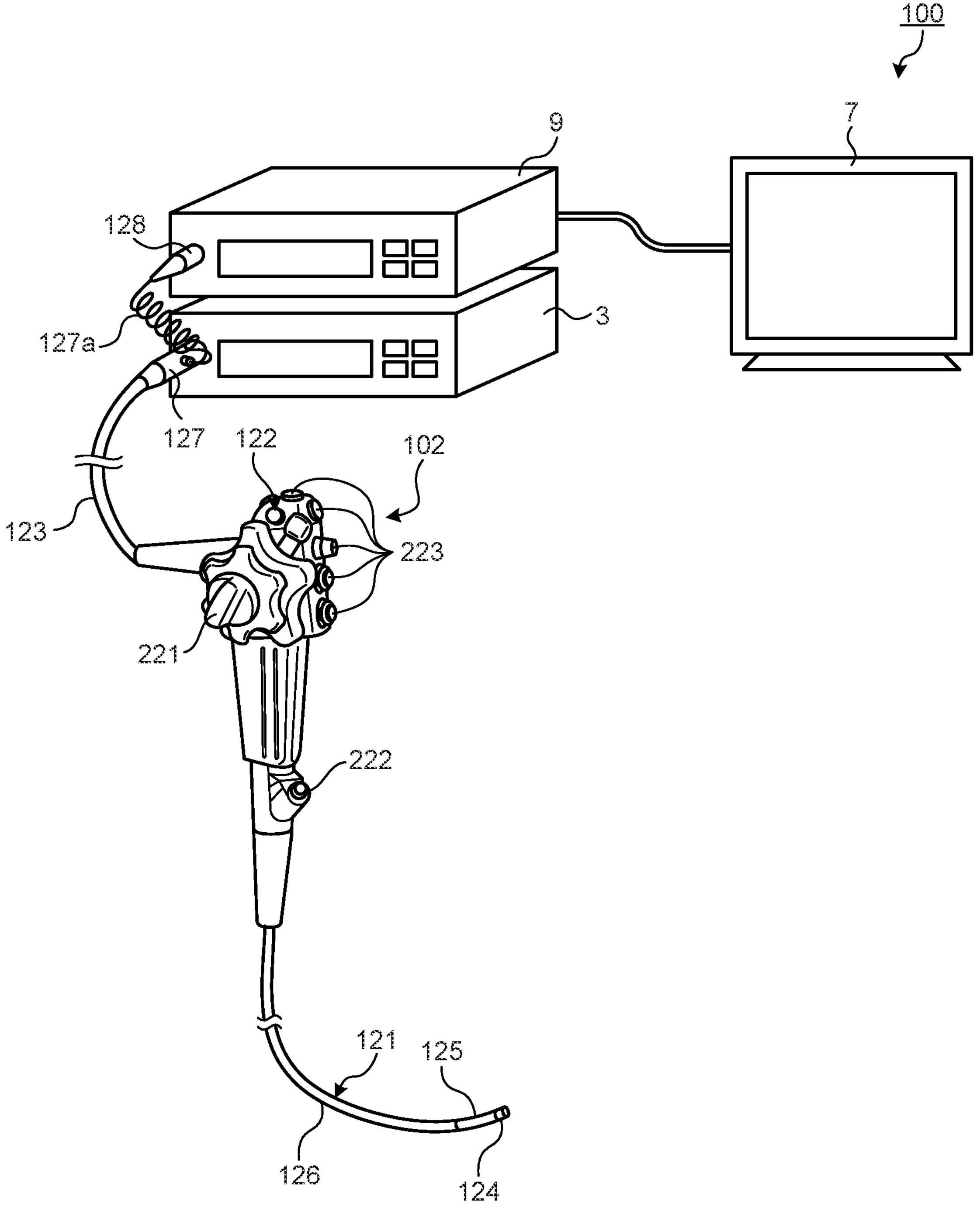
FIG. 26 is a diagram illustrating an overview configuration of an endoscopic system according to a fourth embodiment.
Figure 27:
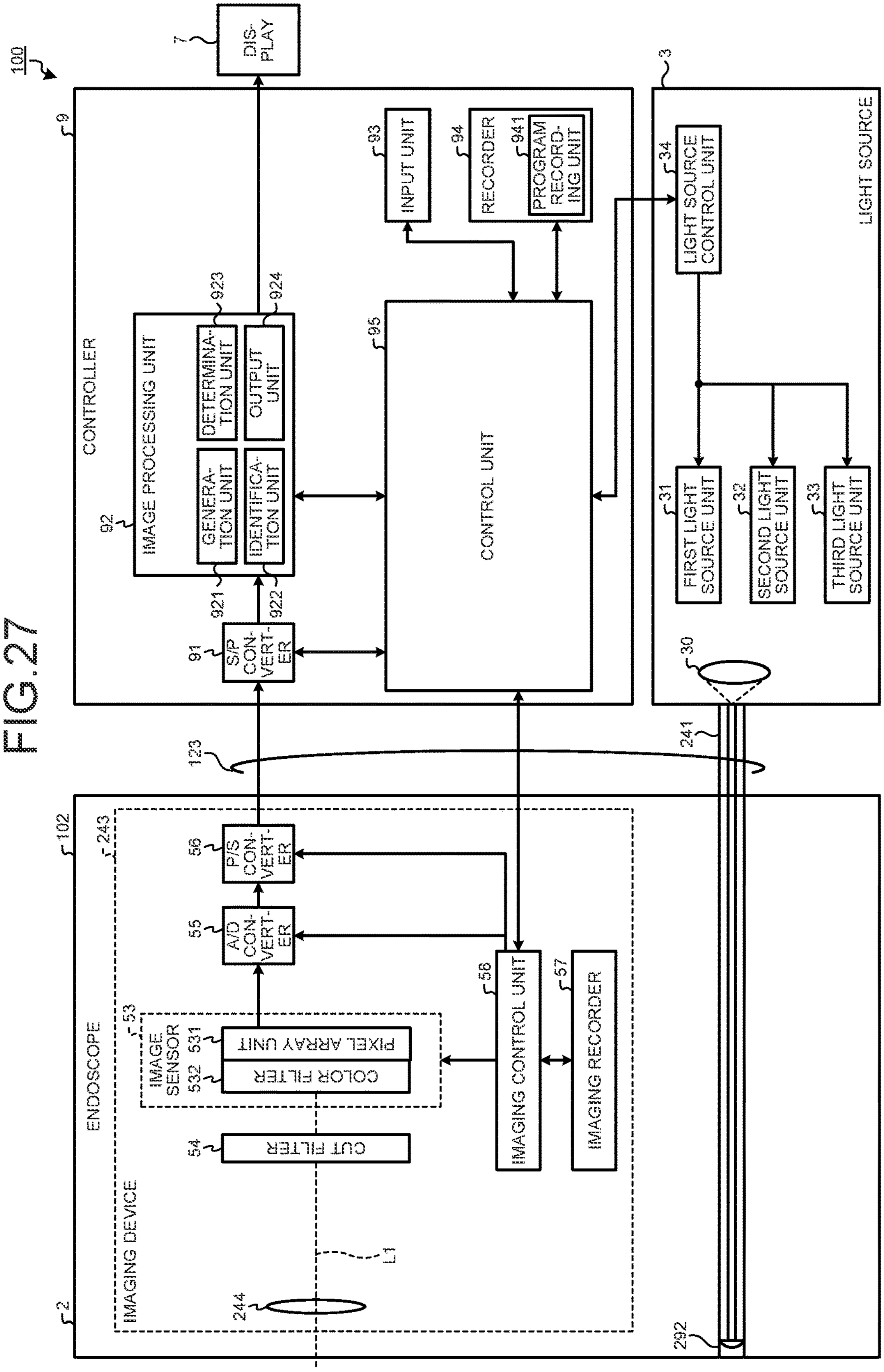
FIG. 27 is a block diagram illustrating a functional configuration of main components of the endoscopic system according to the fourth embodiment.

FIG. 26 is a diagram illustrating an overview configuration of an endoscopic system according to a fourth embodiment. FIG. 27 is a block diagram illustrating a functional configuration of main components of the endoscopic system according to the fourth embodiment.

An endoscopic system 100 illustrated in FIGS. 26 and 27 is inserted into a subject such as a patient to capture an image of the inside of the subject, and the display 7 displays a display image based on the captured image data. A surgical operator such as a doctor observes the display image displayed by the display 7 to examine the presence or absence and the state of each of the bleeding site, the tumor site, and the abnormal region in which the abnormal site appears as the examination target site. Furthermore, a surgical operator such as a doctor inserts a treatment tool such as an energy device into a body of the subject via a treatment tool channel of an endoscope to treat the subject. The endoscopic system 100 includes an endoscope 102 in addition to the light source 3, the display 7, and the controller 9 described above.

Configuration of Endoscope

The configuration of the endoscope 102 is now described. The endoscope 102 generates image data by capturing the inside of the body of the subject, and outputs the generated image data to the controller 9. The endoscope 102 includes an operating unit 122 and a universal cord 123.

An insertion portion 121 has an elongated shape having flexibility. The insertion portion 121 includes a distal end portion 124 incorporating an imaging device to be described later, a bendable bending portion 125 including a plurality of bending pieces, and an elongated flexible tube portion 126 connected to a proximal end side of the bending portion 125 and having flexibility.

The distal end portion 124 is configured using glass fiber or the like. The distal end portion 124 includes a light guide 241 forming a light guide path of the light supplied from the light source 3, an illumination lens 242 provided at the distal end of the light guide 241, and an imaging device 243.

The imaging device 243 includes an optical system 244 for condensing light, the image sensor 53, the cut filter 54, the analog-to-digital (A/D) converter 55, the parallel-to-serial (P/S) converter 56, the imaging recorder 57, and the imaging control unit 58 according to the first embodiment described above. Note that, in the third embodiment, the imaging device 243 functions as a medical imaging device.

The universal cord 123 incorporates at least a light guide 241 and an assembled cable in which one or a plurality of cables are collected. The assembled cable is a signal line for transmitting and receiving signals between the endoscope 102 and the light source 3 and the controller 9, and includes a signal line for transmitting and receiving setting data, a signal line for transmitting and receiving a captured image (image data), a signal line for transmitting and receiving a driving timing signal for driving the image sensor 53, and the like. The universal cord 123 has a connector portion 127 detachable from the light source 3. The connector portion 127 has a coil-shaped coil cable 127*a* extending, and a connector portion 128 detachably attached to the controller 9 at an extending end of the coil cable 127*a*.

The endoscopic system 100 configured as described above performs processing similar to that of the endoscopic system 1 according to the first embodiment described above.

According to the fourth embodiment described above, similarly to the first embodiment described above, the surgical operator can easily grasp the characteristic region (lesion site) being left unremoved.

Fifth Embodiment

Next, a fifth embodiment will be described. In the above-described first to fourth embodiments, the endoscopic system is described, but in the fifth embodiment, a case where the endoscopic system is applied to a surgical microscope system will be described. In the fifth embodiment, the same components as those of the endoscopic system 1 according to the first embodiment described above are denoted by the same reference numerals, and a detailed description thereof will be omitted.

Figure 28:
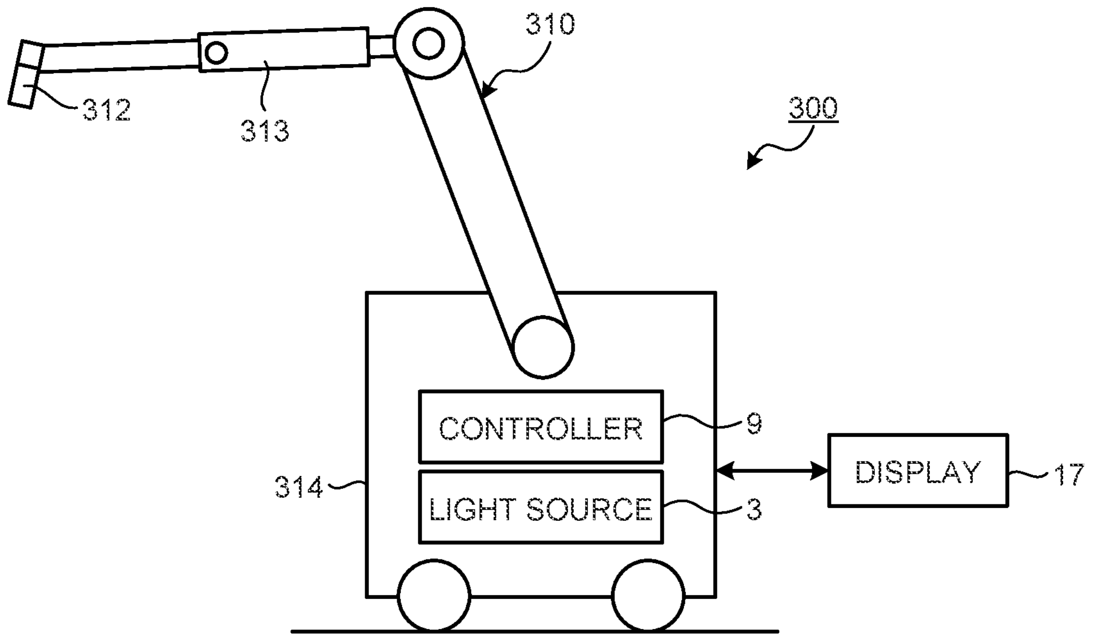
FIG. 28 is a diagram illustrating an overview configuration of a surgical microscope system according to a fifth embodiment.

Configuration of Surgical Microscope System FIG. 28 is a diagram illustrating an overview configuration of a surgical microscope system according to the fifth embodiment; A surgical microscope system 300 illustrated in FIG. 28 includes a microscope device 310 that is a medical imaging device that captures and acquires an image for observing a photographic subject, and a display 7. Note that the display 7 and the microscope device 310 can also be integrally configured.

The microscope device 310 includes a microscope unit 312 that enlarges and captures a minute portion of a photographic subject, a support unit 313 that is connected to a proximal end portion of the microscope unit 312 and includes an arm that rotatably supports the microscope unit 312, and a base unit 314 that rotatably holds the proximal end portion of the support unit 313 and is movable on a floor surface. The base unit 314 includes a light source 3 that generates white light beam, first narrow-band light, second narrow-band light, and the like to be emitted from the microscope device 310 to the photographic subject, and a controller 9 that controls the operation of the surgical microscope system 300. Note that each of the light source 3 and the controller 9 has at least a configuration similar to that of the first embodiment described above.

Specifically, the light source 3 includes a condenser lens 30, a first light source unit 31, a second light source unit 32, a third light source unit 33, and a light source control unit 34. Furthermore, the controller 9 includes a serial-to-parallel (S/P) converter 91, an image processing unit 92, an input unit 93, a recorder 94, and a control unit 95. The base unit 314 may be fixed to a ceiling, a wall surface, or the like to support the support unit 313 instead of being movably provided on the floor surface.

The microscope unit 312 has, for example, a cylindrical shape and includes the above-described medical imaging device inside. Specifically, the medical imaging device has a configuration similar to that of the endoscopic camera head 5 according to the first embodiment described above. For example, the microscope unit 312 includes an optical system 51, a driver 52, an image sensor 53, a cut filter 54, an analog-to-digital (A/D) converter 55, a parallel-to-serial (P/S) converter 56, an imaging recorder 57, and an imaging control unit 58. In addition, a switch that receives an input of an operation instruction of the microscope device 310 is provided on a side surface of the microscope unit 312. A cover glass for protecting the inside is provided on an aperture surface of a lower end portion of the microscope unit 312 (not illustrated). In the surgical microscope system 300 configured as described above, a user such as a surgical operator moves the microscope unit 312, performs a zoom operation, or switches illumination light while operating various switches in a state of holding the microscope unit 312. Note that the shape of the microscope unit 312 is preferably a shape elongated in the observation direction so that the user can easily hold and change the viewing direction. Therefore, the shape of the microscope unit 312 may be a shape other than the columnar shape, and may be, for example, a polygonal columnar shape.

According to the fifth embodiment described above, also in the surgical microscope system 300, similarly to the first embodiment described above, the surgical operator can easily grasp the characteristic region (lesion site) being left unremoved.

Sixth Embodiment

Next, a sixth embodiment will be described. In the above-described first embodiment, the cut filter 54 is provided on the light-receiving surface side (incident surface side) of the G pixel, but in the sixth embodiment, the cut filter 54 is provided on the light-receiving surface side (incident surface side) of each of the R pixel, the G pixel, and the B pixel. Hereinafter, an endoscopic system according to the sixth embodiment will be described. Note that the same components as those of the endoscopic system 1 according to the first embodiment described above are denoted by the same reference numerals, and a detailed description thereof will be omitted.

Functional Configuration of Main Components of Endoscopic System

Figure 29:
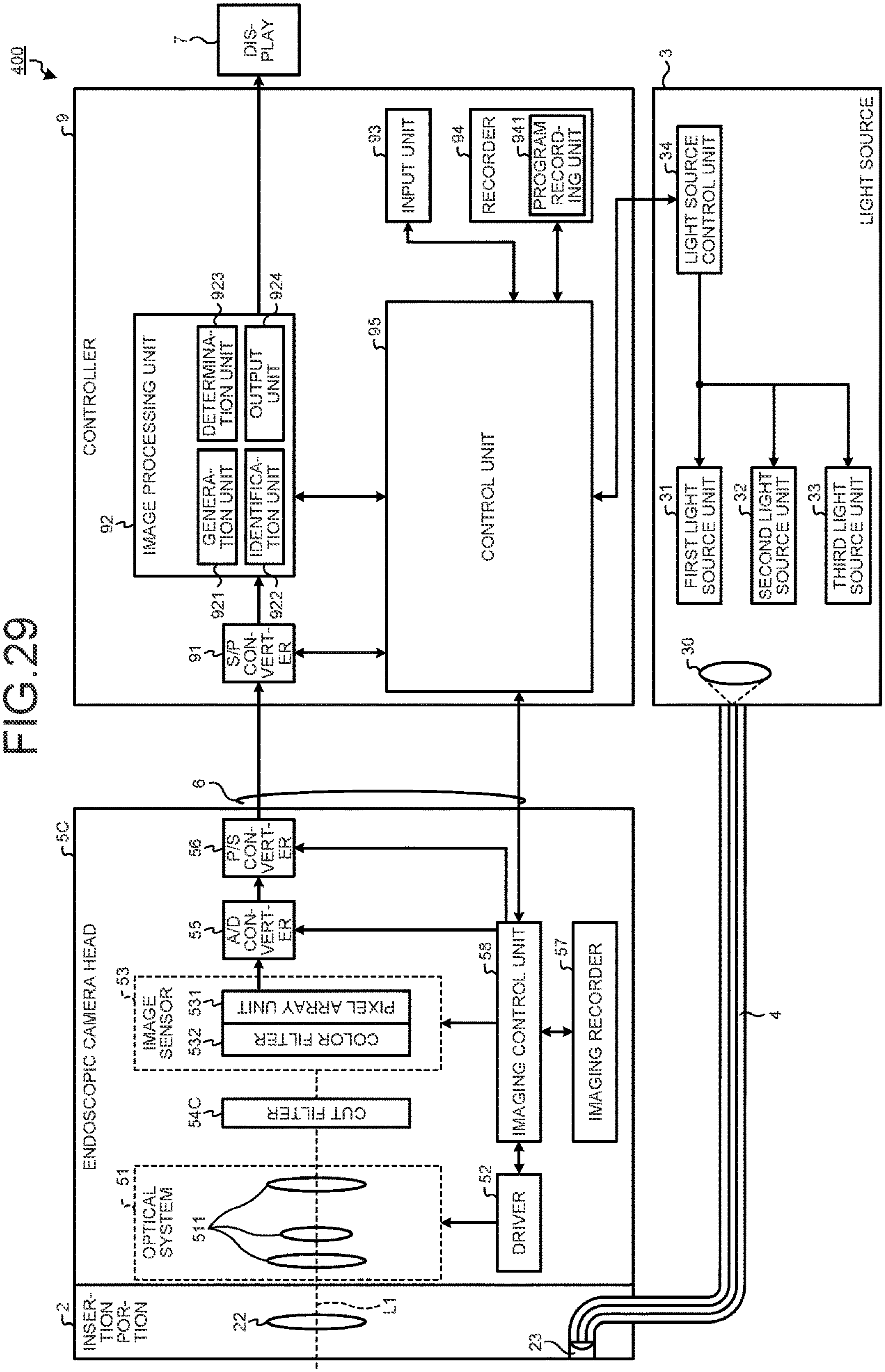
FIG. 29 is a block diagram illustrating a functional configuration of main components of the endoscopic system according to a sixth embodiment.

FIG. 29 is a block diagram illustrating a functional configuration of main components of the endoscopic system according to the sixth embodiment. An endoscopic system 400 illustrated in FIG. 29 includes an endoscopic camera head 5C instead of the endoscopic camera head 5 according to the above-described first embodiment. Furthermore, the endoscopic camera head 5C includes a cut filter 54C instead of the cut filter 54 according to the first embodiment described above.

The cut filter 54C is arranged on the optical axis between the optical system 51 and the image sensor 53. The cut filter 54C blocks most of the light in the short wavelength band including the wavelength band of the excitation light (allows a part of the excitation light to pass through) and allows light in the wavelength bands on the longer wavelength side than the wavelength band with which the most of the light is blocked to pass through.

Figure 30:
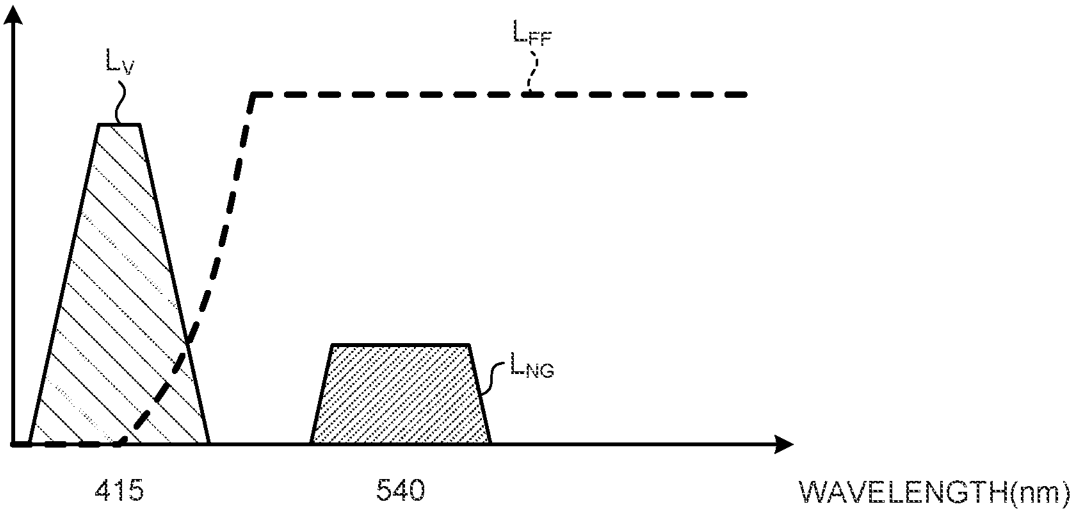
FIG. 30 is a diagram schematically illustrating transmission characteristics of a cut filter according to the sixth embodiment.

FIG. 30 is a diagram schematically illustrating transmission characteristics of a cut filter 54C. In FIG. 30, the horizontal axis indicates the wavelength (nm), and the vertical axis indicates the transmission characteristics. Furthermore, in FIG. 30, a polygonal line $L_{FF}$ indicates the transmission characteristics of the cut filter 54C, a polygonal line $L_V$ indicates the wavelength characteristics of the excitation light, and a polygonal line $L_{NG}$ indicates the wavelength characteristics in the fluorescence of AGEs.

As indicated by the polygonal line $L_{FF}$ in FIG. 30, the cut filter 54C blocks most of the light in the wavelength band of the excitation light (allows a part of the excitation light to pass through) and allows light in the wavelength band on the longer wavelength side than the wavelength band with which the most of the light is blocked to pass through. Specifically, the cut filter 54C blocks most of the light in a wavelength band on the short wavelength side of less than any wavelength in the range of 430 nm to 470 nm, which includes the wavelength band of excitation light, and allows light in a wavelength band on the longer wavelength side than the wavelength band that blocks most of the light to pass through. For example, the cut filter 54C transmits the fluorescence of the AGEs generated by the thermal treatment as indicated by a polygonal line $L_{NG}$.

Overview of Observation Modes

An overview of observation modes executed by the endoscopic system 400 is now described. Moreover, the description below is given in the order of a thermal treatment imaging observation mode, and a normal light imaging observation mode.

Overview of Thermal Treatment Imaging Observation Mode

Figure 31:
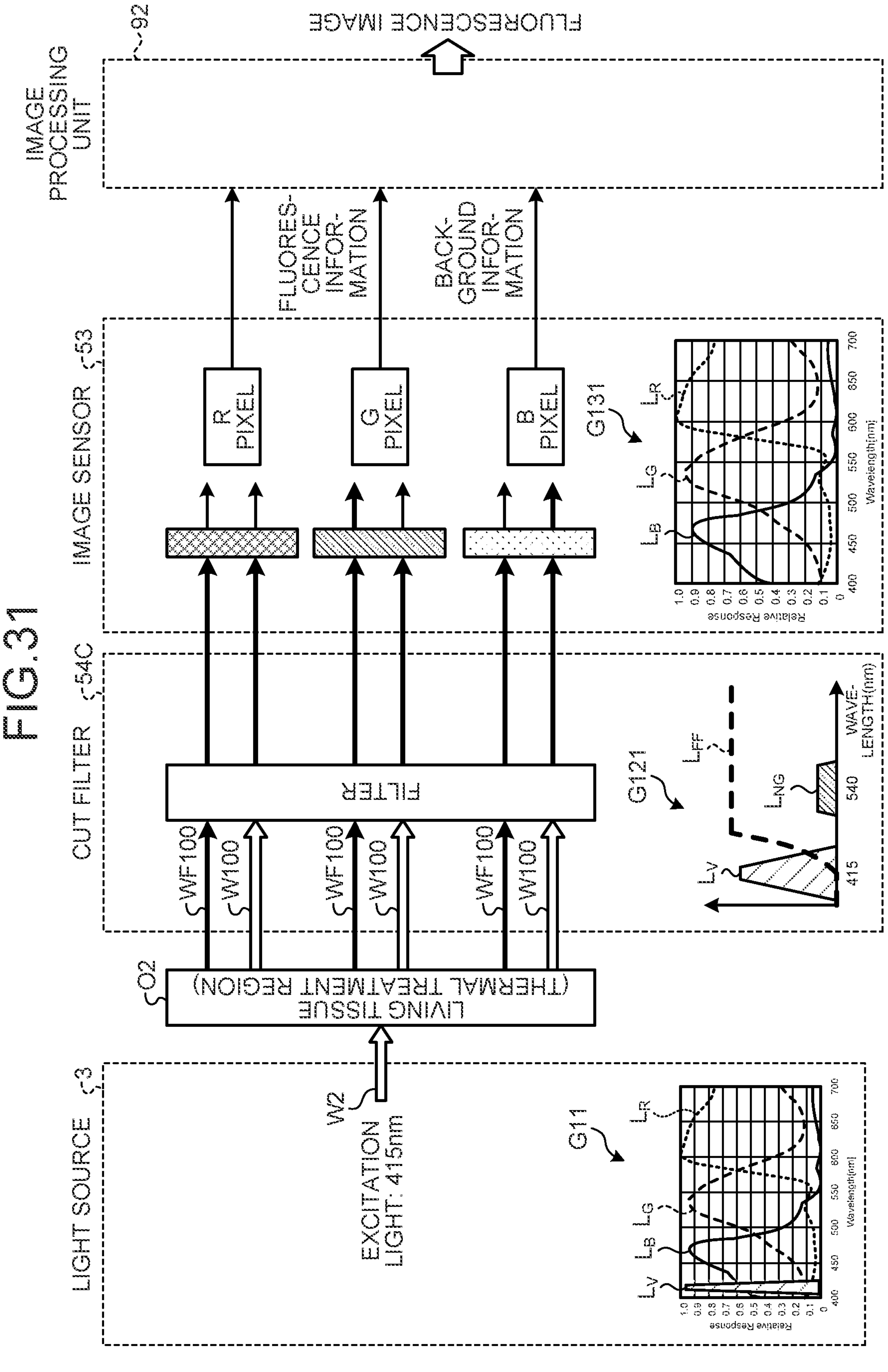
FIG. 31 is a diagram schematically illustrating an image observation principle in a thermal treatment imaging observation mode according to the sixth embodiment.

First, the thermal treatment imaging observation mode will be described. FIG. 31 is a diagram schematically illustrating an image observation principle in a thermal treatment imaging observation mode.

As illustrated in the graph G11 of FIG. 31, the light source 3 first causes the third light source unit 33 to emit light under the control of the controller 9. Thus, a living tissue O2 (thermal treatment region) of a subject that is thermally treated by an energy device or the like is irradiated with the second narrow-band light beam W2, which is excitation light (with a center wavelength of 415 nm). In this case, as illustrated in the graph G121 of FIG. 31, the reflected light (referred hereinafter to as "reflected light beam W100") is blocked by the cut filter 54C, and the intensity thereof is decreased. This reflected light includes at least the component of the excitation light reflected by the living tissue O2 (thermal treatment region) and the return light are blocked by the cut filter 54C. On the other hand, a part of the components on the longer wavelength side than the wavelength band with which most of the reflected light is blocked does not decrease its intensity and is incident on the image sensor 53.

More specifically, as illustrated in the graph G121 of FIG. 31, the cut filter 54C blocks most of the reflected light W100 beam incident on the G pixel, which is the reflected light W100 beam in a wavelength band with the short wavelength band including the wavelength band of the excitation light (allows a part of the excitation light to pass through) and allows light in the wavelength band on the longer wavelength side than the wavelength band with which the most of the light is blocked to pass through. Furthermore, as illustrated in the graph G121 of FIG. 31, the cut filter 54C causes fluorescence WF100 that is auto-luminous by AGEs in the living tissue O2 (thermal treatment region) to be passed through. Thus, the reflected light beam W100 having decreased intensity and the fluorescence WF10 are incident on each of the R pixel, G pixel, and the B pixel.

Further, as illustrated by the polygonal line $L_{NG}$ Of the fluorescence characteristics in the graph G121 of FIG. 31, the G pixel has a sensitivity to fluorescence, but the output value is relatively small due to the minute fluorescence response.

The image processing unit 92 then acquires image data (raw data) from the image sensor 53 of the endoscopic camera head 5C and performs image processing on each signal value of the G pixel and B pixel included in the acquired image data to generate a fluorescence image (pseudo-color image). In this case, the signal value of the G pixel includes information regarding fluorescence emitted from the thermal treatment region. In addition, the B pixel includes information regarding the background from the living tissue of the subject including the thermal treatment region. Therefore, the image processing unit 92 performs processing similar to that of the first embodiment described above to generate a fluorescence image. Specifically, the image processing unit 92 generates a fluorescence image (pseudo-color image) by performing demosaic processing, processing of calculating an intensity ratio for each pixel, processing of determining a fluorescence region and a background region, and image processing of different parameters on each of a color component signal (pixel value) of a pixel located in the fluorescence region and a color component signal (pixel value) of a pixel located in the background region. Then, the image processing unit 92 outputs the thermal treatment image to the display 7. Here, the fluorescence region is a region in which fluorescence information is superior to background information. In addition, the background region refers to a region in which background information is superior to fluorescence information. Specifically, in a case where the intensity ratio between the reflected light component signal corresponding to the background information and the fluorescence component signal corresponding to the fluorescence information included in the pixel is greater than or equal to a predetermined threshold value (for example, greater than or equal to 0.5), the image processing unit 92 determines the region as the fluorescence region, and in a case where the intensity ratio is less than the predetermined threshold value, the image processing unit determines the region as the background region.

As described above, in the thermal treatment imaging observation mode, it is possible to easily observe the living tissue O1 (thermal treatment region) to be subjected to thermal treatment by an energy device or the like.

Overview of Normal Light Imaging Observation Mode

Figure 32:
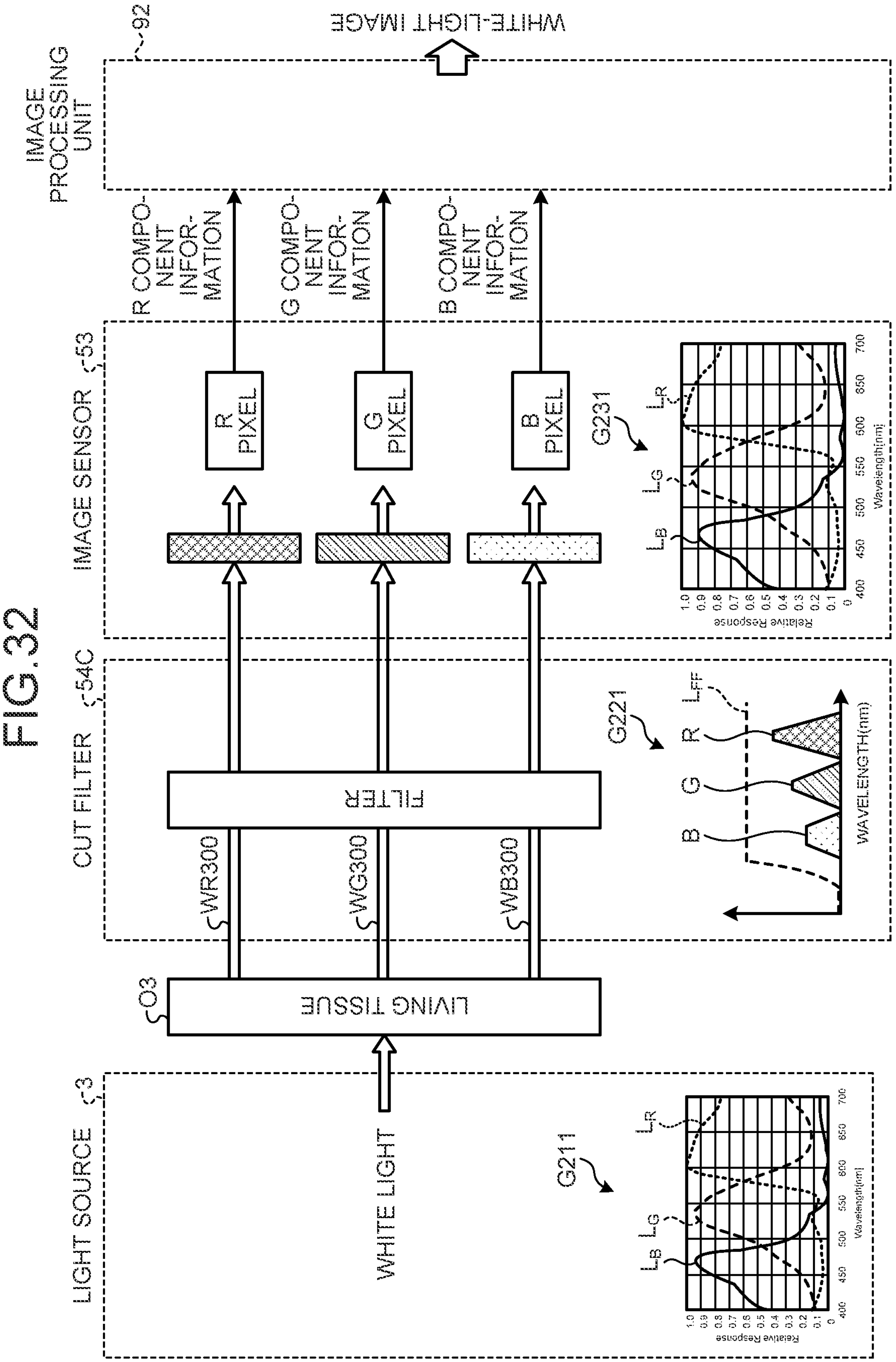
FIG. 32 is a diagram schematically illustrating an image observation principle in a normal light imaging observation mode according to the sixth embodiment.

Next, the normal light imaging observation mode will be described. FIG. 32 is a diagram schematically illustrating an image observation principle in a normal light imaging observation mode.

As illustrated in the graph G211 of FIG. 32, the light source 3 first causes the first light source unit 31 to emit light to irradiate a living tissue O3 of a subject with a white light beam under the control of the controller 9. In this case, a part of the reflected light and return light reflected by the living tissue (hereinafter simply referred to as "reflected light beam WR300, reflected light beam WG300, and reflected light beam WB300") is blocked by the cut filter 54C, and the rest is incident on the image sensor 53. Specifically, as illustrated in the graph G221 of FIG. 32, the cut filter 54C blocks the reflected light beam of a wavelength band with a short wavelength that includes the wavelength band of the excitation light. Thus, as illustrated in the graph G231 of FIG. 34, the component of light in the blue wavelength band incident on the B pixel is smaller than the case where the cut filter 54C is not arranged.

Subsequently, the image processing unit 92 acquires image data (raw data) from the image sensor 53 of an endoscopic camera head 5A and performs image processing on the signal values of each of the R, G, and B pixels included in the acquired image data to generate a white-light image. In this case, the image processing unit 92 performs white balance adjustment processing that adjusts the white balance so that the ratio of the red, green, and blue components is constant because the blue component included in the image data is smaller than that in the white-light imaging observation in the related art.

Thus, in the normal light imaging observation mode, it is possible to observe a natural white-light image even in the case where the cut filter 54C is arranged.

That is, the endoscopic system 400 performs processing similar to that of the above-described first embodiment, determines the background region and the fluorescence region in the thermal treatment imaging observation mode, and applies different image processing parameters to each of the background region and the fluorescence region, thereby generating a fluorescence image in which the fluorescence region is emphasized from the background region and displaying the fluorescent image on the display 7. Furthermore, even in a case where the cut filter 54C is arranged in the normal light imaging observation mode and the narrow-band imaging observation mode, the endoscopic system 400 can generate a white-light image and a pseudo-color image because the component of the light in the blue wavelength band incident on the B pixel and the component of the light in the green wavelength band incident on the G pixel are only smaller than those in a state where the cut filter 54C is not arranged.

According to the sixth embodiment described above, the same effects as those of the first embodiment described above are obtained, and the cut filter 54C as an optical element is provided, so that it is possible to prevent the fluorescence from the heat treatment region from being buried in the reflected light and the return light reflected by the living tissue.

OTHER EMBODIMENTS

Various embodiments can be formed by appropriately combining a plurality of components disclosed in the endoscopic system according to the above-described first to fourth and sixth embodiments or the surgical microscope system according to the fifth embodiment of the present disclosure. For example, some components may be deleted from all the components described in the endoscopic system or the surgical microscope system according to the embodiment of the present disclosure described above. Furthermore, the components described in the endoscopic system or the surgical microscope system according to the embodiment of the present disclosure described above may be appropriately combined.

In addition, in the first to sixth embodiments of the present disclosure, an example of being used for transurethral resection of bladder tumors has been described, but the disclosure is not limited thereto, and can be applied to various treatments of excision of a lesion by, for example, an energy device or the like.

Furthermore, in the endoscopic system or the surgical microscope system according to the first to sixth embodiments of the present disclosure, the above-described "unit" can be replaced with "means", "circuit", or the like. For example, the control unit can be replaced with a control means or a control circuit.

Note that, in the description of the flowcharts in the present specification, the context of processing between steps is clearly indicated using expressions such as "first", "thereafter", and "subsequently", but the order of processing necessary for implementing the disclosure is not uniquely determined by these expressions. That is, the order of processing in the flowcharts described in the present specification can be changed within a range without inconsistency.

Note that the present disclosure can also take the following procedures.

A procedure for the transurethral resection of bladder tumors, including:

- identifying a bladder tumor;
- inserting an endoscope through a urethra of a subject;
- checking a characteristic region including a tumor position by observation using white light;
- excising the characteristic region by thermal treatment with an energy device; and
- checking a cauterized region thermally treated by observing fluorescence in a green light band generated by irradiating advanced glycation end products produced by the thermal treatment with excitation light.

According to the present disclosure, it is possible to easily recognize a characteristic region being left unremoved.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An assistant device comprising:

a processor configured to:

- generate a first image including one or more characteristic regions requiring excision by a surgical operator;
- identify the one or more characteristic regions in the first image;
- generate a second image including one or more cauterized regions produced by applying thermal treatment to a living tissue;
- identify the one or more cauterized regions in the second image;
- superimpose the first image on the second image in a same field of view to determine whether or not a characteristic region not included in the one or more cauterized regions is present; and
- output information indicating a presence of the characteristic region that requires to be cauterized when the characteristic region not included in the one or more cauterized regions is present.

2. The assistant device according to claim 1, wherein the processor is configured to:

- identify the one or more characteristic regions in the first image by extracting a pixel corresponding to the one or more characteristic regions from the first image;
- identify the one or more cauterized regions in the second image by extracting a pixel corresponding to the one or more cauterized regions from the second image; and
- compare the pixel corresponding to the one or more characteristic regions with the pixel corresponding to the one or more cauterized regions to determine whether or not the characteristic region not included in the one or more cauterized regions is present.

3. The assistant device according to claim 1, wherein the processor is configured to generate the second image based on an imaging signal obtained by capturing fluorescence produced by excitation light, the excitation light being applied to excite advanced glycation end products produced by subjecting the living tissue to thermal treatment.

4. The assistant device according to claim 3, wherein the excitation light has a wavelength band ranging from 390 nm to 430 nm,
the fluorescence has a wavelength band ranging from 500 nm to 640 nm, and
the imaging signal is obtained by capturing transmission light that passes through a cut filter configured to block light having a shorter wavelength than 430 nm.

5. The assistant device according to claim 1, wherein the processor is configured to generate the first image based on an imaging signal obtained by capturing a reflected light beam when the living tissue is irradiated with narrow-band light and by capturing a return light beam from the living tissue, the narrow-band light having a narrower wavelength band narrower than a wavelength band of white light.

6. The assistant device according to claim 1, further comprising:
a learned model configured to learn learning data obtained by associating a plurality of biological images with a characteristic region of each of the plurality of biological images, input an imaging signal obtained by capturing a reflected light beam when the living tissue is irradiated with white light and by capturing a return light beam from the living tissue as input data, and output a position of a characteristic region in a captured image corresponding to the imaging signal as output data,
wherein the processor is configured to generate the first image using the learned model and the imaging signal.

7. The assistant device according to claim 1, wherein the processor is configured to generate the first image based on an imaging signal and annotation operation information, the imaging signal being obtained by capturing a reflected light beam when the living tissue is irradiated with white light and by capturing a return light beam from the living tissue, the annotation operation information indicating that the surgical operator performs annotation on a tumor region in a white-light image corresponding to the imaging signal.

8. The assistant device according to claim 1, wherein the processor is configured to determine whether or not each luminance value of pixels of the second image is equal to or greater than a predetermined threshold, and identify one or more pixels having a luminance value equal to or greater than the predetermined threshold as the one or more cauterized regions.

9. The assistant device according to claim 1, wherein the processor is configured to
capture a reflected light and a return light from the living tissue when irradiating the living tissue with a first narrow-band light having a wavelength band narrower than a wavelength band of white light and a second narrow-band light having a wavelength band lower than the wavelength band of the first narrow-band light, thereby generating a first imaging signal, and
generate the first image based on the first imaging signal.

10. The assistant device according to claim 1, wherein the processor is configured to
calculate a hue of each pixel in the first image, and
identify one or more pixels having a hue of a predetermined value as the one or more characteristic regions.

11. The assistant device according to claim 1, wherein the processor is configured to
determine whether or not each pixel of the second image has predetermined luminance or more, and
identify a pixel having the predetermined luminance or more as the cauterized region.

12. An endoscopic system comprising:
an endoscope configured to be inserted into a lumen of a subject;
a light source configured to apply excitation light that excites advanced glycation end products produced by subjecting a living tissue to thermal treatment; and
a controller that is detachable from the endoscope, the endoscope including an image sensor and an optical filter, the image sensor being configured to generate an imaging signal by capturing fluorescence emitted by the excitation light, the optical filter being provided on a light-receiving surface side of the image sensor, the optical filter being configured to block light on a short wavelength side including a part of a wavelength band of the excitation light,
the controller including a processor configured to:
generate a first image including one or more characteristic regions requiring excision by a surgical operator;
identify the one or more characteristic regions in the first image;
generate a second image including one or more cauterized regions produced by applying the thermal treatment to the living tissue;
identify the one or more cauterized regions in the second image;
superimpose the first image on the second image in a same field of view to determine whether or not a characteristic region not included in the one or more cauterized regions is present; and
output information indicating a presence of the characteristic region that requires to be cauterized when the characteristic region not included in the one or more cauterized regions is present.

13. An assistant method executed by an assistant device, the method comprising:
generating a first image including one or more characteristic regions requiring excision by a surgical operator;
identifying the one or more characteristic regions in the first image;
generating a second image including one or more cauterized regions produced by applying thermal treatment to a living tissue;
identifying the one or more cauterized regions in the second image;
superimposing the first image on the second image in a same field of view to determine whether or not a characteristic region not included in the one or more cauterized regions is present; and
outputting information indicating a presence of the characteristic region that requires to be cauterized when the characteristic region not included in the one or more cauterized regions is present.

14. A non-transitory computer-readable recording medium with an executable program stored thereon, the program causing an assistant device to:

generate a first image including one or more characteristic regions requiring excision by a surgical operator;

identify the one or more characteristic regions in the first image;

generate a second image including one or more cauterized regions produced by applying thermal treatment to a living tissue;

identify the one or more cauterized regions in the second image;

superimpose the first image on the second image in a same field of view to determine whether or not a characteristic region not included in the one or more cauterized regions is present; and output information indicating a presence of the characteristic region that requires to be cauterized when the characteristic region not included in the one or more cauterized regions is present.

* * * * *